United States Patent
Sanders et al.

(10) Patent No.: US 8,927,204 B2
(45) Date of Patent: *Jan. 6, 2015

(54) COLORIMETRIC SUBSTRATES, COLORIMETRIC SENSORS, AND METHODS OF USE

(75) Inventors: Mitchell C. Sanders, West Boylston, MA (US); Gerard J. Colpas, Holden, MA (US); Diane L. Ellis-Busby, Lancaster, MA (US); Jennifer M. Havard, Framingham, MA (US)

(73) Assignee: WoundChek Laboratories, Inc., Fall River, MA (US)

( * ) Notice: Subject to any disclaimer, the term of this patent is extended or adjusted under 35 U.S.C. 154(b) by 1959 days.

This patent is subject to a terminal disclaimer.

(21) Appl. No.: 10/576,634

(22) PCT Filed: Nov. 3, 2004

(86) PCT No.: PCT/US2004/036469
§ 371 (c)(1),
(2), (4) Date: Apr. 5, 2007

(87) PCT Pub. No.: WO2005/042771
PCT Pub. Date: May 12, 2005

(65) Prior Publication Data
US 2007/0269851 A1    Nov. 22, 2007

Related U.S. Application Data

(60) Provisional application No. 60/516,688, filed on Nov. 3, 2003, provisional application No. 60/578,502, filed on Jun. 9, 2004.

(51) Int. Cl.
*C12Q 1/00*     (2006.01)
*C12Q 1/37*     (2006.01)
*C12Q 1/04*     (2006.01)

(52) U.S. Cl.
CPC ... *C12Q 1/04* (2013.01); *C12Q 1/37* (2013.01)
USPC .................................................. 435/4; 435/5

(58) Field of Classification Search
CPC ......................................................... C12Q 1/04
USPC ...................................................... 435/4, 18
See application file for complete search history.

(56) References Cited

U.S. PATENT DOCUMENTS

| | | | |
|---|---|---|---|
| 4,242,447 A | 12/1980 | Findl et al. | |
| 5,393,514 A | 2/1995 | Pitner et al. | |
| 5,798,276 A | 8/1998 | Haugland et al. | |
| 5,846,737 A | 12/1998 | Kang | |
| 7,244,583 B2 | 7/2007 | Sanders | |
| 7,566,564 B2 | 7/2009 | Colpas et al. | |
| 8,124,370 B2 | 2/2012 | Sanders et al. | |
| 8,377,651 B2 | 2/2013 | Colpas et al. | |
| 8,541,193 B2 | 9/2013 | Sanders et al. | |
| 8,609,358 B2 | 12/2013 | Sebastian et al. | |
| 2005/0142622 A1 | 6/2005 | Sanders et al. | |
| 2013/0316369 A1 | 11/2013 | Colpas et al. | |
| 2014/0051089 A1 | 2/2014 | Sanders et al. | |

FOREIGN PATENT DOCUMENTS

| | | |
|---|---|---|
| EP | 0 122 028 A1 | 10/1984 |
| JP | 11-178567 | 7/1999 |
| WO | WO 99/38995 A1 | 8/1999 |
| WO | WO 02 06821 A2 | 1/2002 |
| WO | WO 03 063693 A2 | 8/2003 |
| WO | WO 2005/042771 A2 | 5/2005 |

OTHER PUBLICATIONS

Asai et al. "A colorimetric assay for plasma antithrombin III using a new synthetic peptide substrate (PS-915)", Clinica Chimica Acta, 1984, 144:163-171.*
Kulisek et al. "A chromogenic assay for the detection of plasmin generated by plasminogen activator immobilized on nitrocellulose using a para-nitroanilide synthetic peptide substrate", Anal. Biochem., 1989, 177:78-84.*
Graham et al. "Towards genetic based insect resistance in strawberry using the cowpea trypsin inhibitor gene", Ann. Appl. Biol. 1995, 127:163-173.*
Wolf et al. "Soluble, dye-labeled substrates for a micro-plate assay of proteinase activity", J of Microbiological Methods, 1996, 25:337-342.*
Wang et al. "Solid-phase synthesis of peptide vinyl sulfones as potential inhibitors and activity-based probes of cysteine proteases", Organic Letters, 2003, 5(5):737-740.*
FDA approval evidence:3 pages. 2010.*
Yolken, Robert H., "Enzymic Analysis for Rapid Detection of Microbial Infection in Human Body Fluids: An Overview," Clin. Chem. 27(9): 1490-1498 (1981).
Bowie, J.U., et al., "Deciphering the Message in Protein Sequences: Tolerance to Amino Acid Substitutions," *Science* 247:1306-1310 (1990).
Cunningham, B.C. and J.A. Wells, "High-Resolution Epitope Mapping of hGH-Receptor Interactions by Alanine-Scanning Mutagenesis," *Science* 244:1081-1085 (1989).
Karlin, S. and S.F. Althschul, "Applications and Statistics for Multiple High-Scoring Segments in Molecular Sequences," *Proc. Natl. Acad. Sci. USA* 90:5873-5877 (1993).

* cited by examiner

*Primary Examiner* — Bin Shen
(74) *Attorney, Agent, or Firm* — McDonnell, Boehnen, Hulbert & Berghoff, LLP

(57) ABSTRACT

Described herein is a substrate comprising at least one colorimetric component attached to a peptide, as well as methods for detecting a modification of said substrate. Also described are methods of detecting the presence or absence of a protein, for example, a protein produced by a microorganism, by contacting a substrate with a sample. If the sample contains the protein of interest, the substrate is modified and a visible color change results, indicating the presence or absence of the protein in the sample. The present invention also features biosensors and kits for detecting the presence or absence of microorganisms and/or proteins in a sample.

14 Claims, 8 Drawing Sheets
(3 of 8 Drawing Sheet(s) Filed in Color)

COLORIMETRIC SUBSTRATES, COLORIMETRIC SENSORS, AND METHODS OF USE

RELATED APPLICATIONS

This application is the U.S. National Stage of International Application No. PCT/US2004/036469, filed Nov. 3, 2004, published in English, and claims priority under 35 U.S.C. §119 or 365 to U.S. Provisional Application No. 60/516,688, filed Nov. 3, 2003 as well as U.S. Provisional Application 60/578,502, filed Jun. 9, 2004. The entire teachings of the above applications are incorporated herein by reference,

BACKGROUND OF THE INVENTION

Infection of wounds is a major source of healthcare expenditure in the United States. Approximately 5% of all surgical wounds become infected with microorganisms, and that figure is considerably higher (~10-20%) for patients undergoing abdominal surgery. Bacterial species, such as *Staphylococci*, are the most frequently isolated organisms from infected wounds. This is probably because humans are the natural reservoir for *Staphylococci* in the environment, with up to 50% of the population colonized at any given time. Colonization rates are significantly higher in the hospital setting, both among healthcare workers, and among patients. Moreover, the colonizing organisms in the hospital environment are likely to be resistant to many forms of antimicrobial therapy, due to the strong selective pressure that exists in the nosocomial environment, where antibiotics are frequently used. *Staphylococci* are usually carried as harmless commensals, however given a breach in the epidermis, they can cause severe, even life threatening infection.

*Staphylococci* are the most common etiologic agents in surgical wound infections; others include, but are not limited to, *Streptococcus pyogenes, Pseudomonas aeruginosa, Enterococcusfaecalis, Proteus mirabilis, Serratia marcescens, Enterobacter clocae, Acetinobacter anitratus, Klebsiella pneumoniae,* and *Escherichia coli.*

Post-surgical infection due to microorganisms is a significant concern of hospitals. The most common way of preventing such infection is to administer prophylactic antibiotic drugs. While generally effective, this strategy has the unintended effect of breeding resistant strains of bacteria. The routine use of prophylactic antibiotics should be discouraged for the very reason that it promotes the growth of resistant strains.

Rather than using routine prophylaxis, a better approach is to practice good wound management, i.e., keep the area free from bacteria before, during, and after surgery, and carefully monitor the site for infection during healing. Normal monitoring methods include close observation of the wound site for slow healing, signs of inflammation and pus, as well as measuring the patient's temperature for signs of fever. Unfortunately, many symptoms are only evident after the infection is already established. Furthermore, after a patient is discharged from the hospital he/she becomes responsible for monitoring their own healthcare, and the symptoms of infection may not be evident to the unskilled patient.

A method, system, or biosensor that can detect the early stages of infection before symptoms develop would be advantageous to both patients and healthcare workers. Such a method, or biosensor, should be sensitive to low levels of microorganisms present in a wound to facilitate early detection. If a patient can accurately monitor the condition of a wound after discharge, then appropriate antimicrobial therapy can be initiated early enough to prevent a more serious infection.

SUMMARY OF THE INVENTION

It has been found that substrates can be labelled in order to produce a visible color change when modified by a protein. It has also been found that molecules (e.g., proteins secreted by microorganisms, expressed on the cell surface of microorganisms, or expressed on the surface of a cell infected with a virus or prion) can serve as markers for the detection of the presence or absence of a microorganism in a sample, for example, a wound or body fluid. Accordingly, the present invention features substrates that are modified by proteins, methods of detecting such a modification, methods for detecting proteins, and articles incorporating said substrates.

There are many embodiments to this invention. In some embodiments, this invention includes a substrate comprising at least one calorimetric components attached to a peptide. The substrate can be attached to a solid support. A "colorimetric component" is defined herein as any component that provides color or fluorescence such as, but not limited to, a dye.

In some embodiments, this invention includes a substrate comprising at least two colorimetric components attached to a peptide, wherein the colorimetric components include at least two different colors. In some embodiments, the substrate comprising at least one calorimetric component is attached to a solid support that is colored.

Encompassed by this invention are methods of detecting the modification of a substrate described herein. In one example, the method comprises the steps of a) exposing a sample to the substrate under conditions that will result in a modification of the substrate and b) detecting the modification or an absence of the modification. In some embodiments, the substrate comprises a peptide with at least one colorimetric component. More specifically, the substrate is attached to a solid support. The modification comprises cleaving at least a portion of the substrate, wherein the portion includes one of the colorimetric components and the cleaving results in a detectable signal (e.g., a visible color change). For instance, the colorimetric component of a substrate with one colorimetric component can be cleaved from the substrate and the colorimetric component can diffuse away from the substrate. Hence, the modification of the substrate would be signaled by the loss of color.

In another example, the colorimetric component of a substrate with one colorimetric component can be cleaved from the substrate and the calorimetric component can be collected on a collector. In some embodiments, the collector is a capture membrane or support that would change color as a result of the cleaved substrate being collected by the collector. Hence, the modification of the substrate would be signaled by a color change on the capture membrane that is in proximity to the substrate.

In another example, the substrate comprises two colorimetric components, one of the colorimetric components can be a first color, for example, blue, and a second colorimetric component can be a second color, for example, yellow. When present on the same substrate, the unmodified substrate can appear green. If that same substrate is modified (e.g., such as enzymatic cleavage of the yellow calorimetric component from the substrate) the substrate can appear blue. Hence the modification of the substrate would be signaled by a change in color from green to blue.

As further described herein, a substrate with one colorimetric component can be attached to a solid support that is colored. The peptide colorimetric component can be a first color, such as yellow, and the solid support can be a second color, such as blue. The combination of the solid support with the unmodified substrate can appear green. If the substrate is modified (e.g., such as enzymatic cleavage of the yellow calorimetric component from the substrate), the combination of the solid support and the modified substrate will appear blue. Hence the modification of the substrate would be signaled by a change in color from green to blue.

In other embodiments, the invention includes a method for detecting the presence or absence of an enzyme in a sample using methods described herein. As described herein, the enzyme can be specifically produced or secreted by a microorganism. Thus, detection of the enzyme correlates with the presence, or absence, of the microorganism.

In further embodiment, this invention includes biosensors for detecting the presence or absence of a protein, enzyme, or a microorganism using the methods described herein.

In still another embodiment, this invention includes a kit for detecting a protein, an enzyme, or a microorganism. The kit can comprise a biosensor for detecting the presence or absence of, for example, a microorganism in a sample and at least one reagent for detecting the microorganism. The biosensor can comprise a solid support and at least one detectably labeled substrate, wherein the detectably labeled substrate includes a peptide that specifically reacts with an enzyme, and the substrate further comprises one or more calorimetric components attached to the peptide. The detectably labeled substrate can be bound to the solid support. Optionally, the kit includes a collector.

As described herein, the present invention allows for the detection of proteins, enzymes and microorganisms, including those that cause infections. This invention can be used advantageously in a diverse range of roles, including providing utility in a healthcare setting. For example in a healthcare setting, this invention will allow a user to identify the presence of microorganisms in a wound so that prophylactic measures can be taken before the infection is established. This allows for the selective applications of prophylactic drugs that can reduce some negative side effects of their use, such as breeding resistant strains of microorganisms. Another example of the utility provided by this invention is that it allows a patient to monitor the condition of a wound after he or she has been discharged from a hospital so that he/she may seek medical care or take prophylactic measures if a pathogenic microorganism is detected.

The invention provides for a rapid and low cost detection of proteins, enzymes, or microorganisms in a sample based on modification of a substrate that results in a detectable color change, eliminating the need for expensive equipment to detect a modification of the substrate. The raw materials needed to practice this invention are inexpensive. Additionally, the methods and articles of this invention allow a portable means for detecting the presence of microorganisms, eliminating the need to conduct detection or portions of detection in a laboratory or hospital setting.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
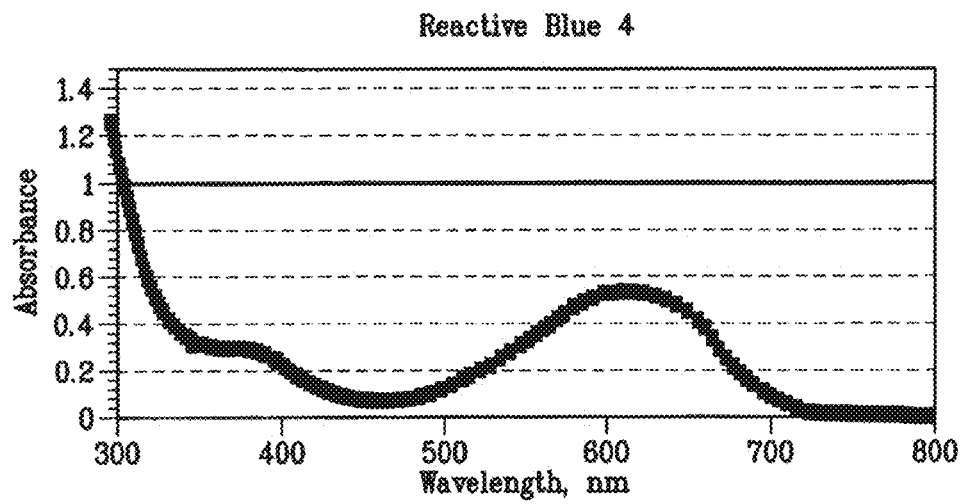
FIG. 1 illustrates the spectra of Reactive Blue 4 in water.

The present invention encompasses compositions and methods useful for the detection of the presence or absence of a protein, enzyme, or a microorganism in a sample. This invention includes a substrate, typically a protein or peptide, comprising a colorimetric component that produces a detectable signal that indicates when the substrate has undergone a modification. The modification can be the result of the substrate contacting a protein, such as an enzyme, and resulting in the modification of the substrate by, for example, enzymatic cleavage.

In some embodiments, the detectable signal includes a visual signal or a visible color change. As used herein, a "visible signal" includes a color change that is perceptible without any kind of detection equipment or enhancing equipments, such as a fluorometer. In other embodiments, the detectable signal is a change in color from one nonfluorescent color or hue to another.

In some embodiments, the invention includes a substrate comprising at least one calorimetric component attached to a peptide. In further embodiments, the substrate is attached to a solid support. In some embodiments, the peptide is one that will undergo a modification when it interacts with a protein. For example, the protein can be an enzyme and the modification can include the enzyme cleaving the peptide. In some embodiments, the peptide is synthetic, while in others it is naturally occurring.

In some embodiments, the peptide can be used directly to detect the presence of a specific protease or indirectly by the use of a signal amplification procedure in which a reporter enzyme is conjugate with a specific peptide and the hydrolysis leads to the activation of a catalytic process leading to a detectable signal (e.g. a visible color change).

Peptides

Examples of peptides include those substrates described herein, as well as those peptides known in the art to undergo modification by interaction with a protein. U.S. patent application Ser. No. 09/848,781, filed May 3, 2001, by Mitchell C. Sanders, entitled A Device for Detecting Bacterial Contamination and Method of Use and U.S. Provisional Application No. 60/383,847, filed May 28, 2002, by Mitchell C. Sanders, et al., entitled Method for Detecting Microorganisms describe such peptides and their teachings are incorporated herein in their entirety.

Specific examples of a suitable peptide can include:
LLGDFFRKSKEKIGKEFKRIVXRIKDFL-RNLVPRTES (referred to herein as "SEQ ID NO: 1"), wherein the "X" member of SEQ ID NO: 1 can be any amino acid;
KAAHKSALKSAE (referred to herein as "SEQ ID NO: 2" or "Papa1");
KKASEAAHKSALKSAE (referred to herein as "SEQ ID NO: 3" or "Papa2");
CHHHASEAAHKSALKSAE (referred to herein as "SEQ ID NO: 4" or "Papa3");
KHLGGGALGGGAKE (referred to herein as "SEQ ID NO: 5" or"Pala1");
KHLGGGGGAKE (referred to herein as "SEQ ID NO: 6" or "Papg1");
ACCDEYLQTKE (referred to herein as "SEQ ID NO: 7" or "P1");
ADTVEPTGAKE (referred to herein as "SEQ ID NO: 8" or "P2");
KLPHKLSWSADNP (referred to herein as "SEQ ID NO: 9" or "P3");
PVPSTPPTPSPSTP (referred to herein as "SEQ ID NO: 10" or "A1");
NMLSEVERE (referred to herein as "SEQ ID NO: 11" or "M1");
KQNMLSEVERADTE (referred to herein as "SEQ ID NO: 12" or "M2");
NEAIQEDQVQYE (referred to herein as "SEQ ID NO: 13" or "Ssp1");
EIKVEENEAIQK (referred to herein as "SEQ ID NO: 14" or "Ssp2" or "SAP2");
DSRPVRRRRRPRVSK (referred to herein as "SEQ ID NO: 15" or "T1");
KVSRRRRRGGD (referred to herein as "SEQ ID NO: 16" or "T2");
KKASEVSRRRRRGGK (referred to herein as "SEQ ID NO: 17" or "T3");
CHHHASEVSRRRRRGGK (referred to herein as "SEQ ID NO: 18" or "T4");
KEKIGKEFKRIVQE (referred to herein as "SEQ ID NO: 19" or "LL1");
KVQRIKDFLRNLVE (referred to herein as "SEQ ID NO: 20" or "LL2");
EAAGAMFLEAIPK (referred to herein as "SEQ ID NO: 21" or "CPI1");
EGAMFLEAIPMSIPK (referred to herein as "SEQ ID NO: 22" or "CPI2");
CGAMFLEAIPMSIPAAAHHHHH (referred to herein as "SEQ ID NO: 23" or "CPI3");
KARRRRGGGAMFLEAIPMSIPCGC (referred to herein as "SEQ ID NO: 24" or "CPI4");
VSRRRRRGGDGDGC (hereafter referred to as "SEQ ID NO: 25" or "JMH001");
GGDGDGC (referred to herein as "SEQ ID NO: 26" or "JMH002");
VSRRRRRGGDGKGDAC (referred to herein as "SEQ ID NO: 27" or "JMH003");
NEAIQEDQVQARRAKARRAC (referred to herein as "SEQ ID NO: 28" or "JMH004");
QVQARRAKARRAC (referred to herein as "SEQ ID NO: 29" or "JMH005");
GGDGKGDAC (referred to herein as "SEQ ID NO: 30" or "JMH006");
QVQARRRAKARRRAC (referred to herein as "SEQ ID NO: 31" or "JMH007");
VSRRRRRGGKGC (referred to herein as "SEQ ID NO: 32" or "JMH008");
SVTRRRRRGGRASGGC (referred to herein as "SEQ ID NO: 33" or "DEB001");
SEAIQEDQVQYCAAAHHHHH (referred to herein as "SEQ ID NO: 34" or "SSP3");
KARRRRRGGDGDGCGC (referred to herein as "SEQ ID NO: 35" or "T5");
HHHHHSRRRRRGGCGC (referred to herein as "SEQ ID NO: 36" or "T6");
HHHHHSVQRIKDFLRNLVCGC (referred to herein as "SEQ ID NO: 37" or "LL3");
RRRRRSVQRIKDFLRNLVCGC (referred to herein as "SEQ ID NO: 38" or "LL4");
HHHHHAAHKSALKSACGC (referred to herein as "SEQ ID NO: 39" or "Papa4");
RRRRRAAKSALKSACGC (referred to herein as "SEQ ID NO: 40" or "Papa5");

Alt derived peptides, for example, PGTKLYTVPW-pyrene (which can bind to the surface of *staphylococci* bacteria; the sequence PGTKLYTVPW is referred to herein as "SEQ ID NO: 41");

peptidoglycans, for example, N-acetylglucosamine-[b-1, 4-N acetylmuramic acid, N-acetylmuramyl-L-alanine, or lipoteichoic acid; and a lipid vesicle containing dye for the detection of hemolysin (many hemolysins form ordered protein complexes that are pore forming toxins, and can be detected by the release of dye from a lipid vesicle followed by diffusion of the dye onto a hydrophobic solid substrate). In some embodiments of the invention, the "X" member of SEQ ID NO:1 is ornithine.

Such substrates described herein can be obtained from commercial sources, such as Sigma-Aldrich, Corp. (St. Louis, Mo.), or can be produced (e.g., isolated, purified, or synthesized) using methods known to those of skill in the art.

In some embodiments, the peptide that undergoes modification through interaction with a protein comprises an amino acid sequence, such as one of the sequences listed herein or a sequence having at least 50%, 60%, 70%, 80%, 85%, 90%, 95%, or 99% sequence identity to one of the sequences listed herein, as determined using a sequence comparison program and parameters described herein.

In some embodiments, additional side groups are attached to one of the amino acids of the peptide chain. For example, DEB001 can include a benzyl ether protecting group bound to one or more of the serine acids on the peptide chain. Protecting groups are chemical groups that are used to protect an amino acid from reacting with a colorimetric component. The use of protecting groups allows for labeling of the same type of amino acid in one peptide with two colorimetric components. For example, one serine group in DEB001 can be protected with a benzyl ether group and the unprotected serine can be reacted with one colorimetric component. The protecting group can be removed and the second serine can be reacted with a different color component, thereby creating a substrate with two different color components.

The peptides of the invention also encompass fragments and sequence variants of the peptides described above. Variants include a substantially homologous peptide encoded by the same genetic locus in an organism, i.e., an allelic variant, as well as other variants. Variants also encompass peptides derived from other genetic loci in an organism. Variants also include peptides substantially homologous or identical to these peptides but derived from another organism (i.e., an ortholog), produced by chemical synthesis, or produced by recombinant methods.

The percent identity of two amino acid sequences can be determined by aligning the sequences for optimal comparison purposes (e.g., gaps can be introduced in the sequence of a first sequence). The amino acids at corresponding positions are then compared, and the percent identity between the two sequences is a function of the number of identical positions shared by the sequences (i.e., % identity=# of identical positions/total # of positions×100). In certain embodiments, the length of the amino acid sequence aligned for comparison purposes is at least 30%, preferably, at least 40%, more preferably, at least 60%, and even more preferably, at least 70%, 80%, 90%, or 100% of the length of the reference sequence. The actual comparison of the two sequences can be accomplished by well-known methods, for example, using a mathematical algorithm. A preferred, non-limiting example of such a mathematical algorithm is described in Karlin et al., 90 PROC. NAT'L ACAD. SCI. USA 5873-77 (1993), which is incorporated herein by reference. Such an algorithm is incorporated into the BLAST programs (version 2.2) as described by Schaffer et al., 29 NUCLEIC ACIDS RES. 2994-3005 (2001), which is incorporated herein by reference. When utilizing BLAST and Gapped BLAST programs, the default parameters of the respective programs can be used. In one embodiment, the database searched is a non-redundant database, and parameters for sequence comparison can be set at: no filters; Expect value of 10; Word Size of 3; the Matrix is BLOSUM62; and Gap Costs have an Existence of 11 and an Extension of 1.

In another embodiment, the percent identity between two amino acid sequences can be determined by using the GAP program in the GCG software package (available from Accelrys, Inc. of San Diego, Calif., at www.accelrys.com, as of Aug. 31, 2001) using either a Blossom 63 matrix or a PAM250 matrix, and a gap weight of 12, 10, 8, 6, or 4 and a length weight of 2, 3, or 4. In yet another embodiment, the percent identity between two nucleic acid sequences can be determined using a gap weight of 50 and a length weight of 3. Other preferred sequence comparison methods are described herein.

The invention also encompasses peptides having a lower degree of identity but having sufficient similarity so as to perform one or more of the same functions performed by a peptide encoded by a nucleic acid molecule of the invention (e.g., the ability to act as a substrate for a protein produced by a microorganism). Similarity is determined by conserved amino acid substitution. Such substitutions are those that substitute a given amino acid in a peptide by another amino acid of like characteristics. Conservative substitutions are likely to be phenotypically silent. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., 247 SCIENCE 1306-10 (1990), which is incorporated herein by reference.

Functional variants can also contain substitution of similar amino acids that result in no change or an insignificant change in function. Alternatively, such substitutions may positively or negatively affect function to some degree. Non-functional variants typically contain one or more non-conservative amino acid substitutions, deletions, insertions, inversions, or truncations or a substitution, insertion, inversion, or deletion in a critical residue or critical region.

Amino acids in a peptide of the present invention that are essential for modification of a substrate can be identified by methods known in the art, such as site-directed mutagenesis or alanine-scanning mutagenesis (Cunningham et al., 244 SCIENCE 1081-85 (1989), which is incorporated herein by reference). The latter procedure introduces a single alanine mutation at each of the residues in the molecule (one mutation per molecule).

The invention also includes peptide fragments of the amino acid sequence of the various above-mentioned peptides or functional variants thereof. For example, fragments can be derived from a polypeptide comprising Pala1. Useful fragments include those that retain the ability to act as substrates for a protein produced by a microorganism.

Fragments can be discrete (not fused to other amino acids or peptides) or can be within a larger peptide. Further, several fragments can be comprised within a single larger peptide. In one embodiment, a fragment designed for expression in a host can have heterologous pre- and pro-peptide regions fused to the amino terminus of the peptide fragment and an additional region fused to the carboxyl terminus of the fragment.

The peptide of the substrate can be produced using standard recombinant protein techniques (See, e.g., AUSUBEL ET AL., CURRENT PROTOCOLS IN MOLECULAR BIOLOGY (1998), the entire teachings of which are incorporated herein by reference). In addition, the proteins of the present invention can also be generated using recombinant techniques. By testing with an ample supply of the protein to be detected and the substrate, the exact site of modification can be determined and a more specific substrate for that protein can be defined, if so desired. This substrate can also be used to assay for the presence of microorganisms of interest.

Colorimetric Components

The substrates are labeled with at least one colorimetric component. Typically, the colorimetric component is a reactive dye capable of attachment to a substrate, protein, or peptide. In some embodiments, the substrates are labeled with at least two calorimetric components (e.g., at least 2, 3, 4, 5, 7, 10, 15, or more colorimetric components. The colorimetric components produce a signal (e.g., a visible change in color) if the substrate is modified (e.g., cleavage of the peptide and/or one or more colorimetric components from the substrate). In this way, the colorimetric components act as a label or tag to indicate the presence or absence of the modification. In some embodiments, the signal is a visible change in color. In other embodiments, the signal is a change in color that is detectable within the visible band of the light spectrum (e.g., from ~700 nm to ~400 nm). By attaching a larger number of colorimetric components to the substrate, a more visible color or color change can be produced. In further embodiments, the substrates are labeled with at least two dissimilar calorimetric components. Such embodiments allow for the possibility of producing two or more different changes of hue.

Many types of dyes, for instance reactive dyes and fiber reactive dyes (referred to herein simply as "reactive dyes;" reactive dyes can be colorimetric or fluorescent), are available commercially (from dye manufacturers such as DyStar Textilfarben GmbH & Co. Deutschland KG, Frankfurt, Germany, and chemical companies, such as Sigma Aldrich, Acros, Molecular Probes, and ICN) and are suitable for use as colorimetric components. The type or specific species of dye(s) selected for a detection method, application, or article of manufacture will depend on the properties of the dye (e.g., a molar extinction coefficient) and the environment in which it is to be used.

Reactive Dyes are colored compounds that contain one or two reactive groups capable of forming covalent bonds between the dye and a protein, peptide, substrate, calorimetric components, a solid support, or a collector. Approximately 80% of all reactive dyes are based on the azo chromophore. Fiber reactive dyes are colored compounds that have a reactive group capable of forming a covalent bond with a fiber. These dyes have been historically used in the textile industry. Examples of other suitable dyes include those that are approved for use in foods, drugs, cosmetics, or medical devices (e.g., contact lenses or sutures) by the U.S. Food and Drug Administration (e.g., Erioglaucine, Reactive Black 5, Reactive Blue 21, Reactive Orange 78, Reactive Yellow 15, Reactive Blue 19, Reactive Blue 4, Reactive Red 11, Reactive Yellow 86, Reactive Blue 163, Reactive Red 180); mono- and dihalogentriazine dyes (e.g., mono- and di-fluorotriazine dyes; mono- and di-chlorotriazine dyes; mono-(m'-carboxypyridinium) triazines; Reactive Blue 4; Reactive Yellow 86; dyes in the PROCION® line of dyes, dyestuffs, and coloring matters, which are available from BASF; and the CIBACRON™ line of coal tar colors, which are available from Ciba-Geigy); 2,4,5 trihalogenopyriminidines; 2,3 dihaloquinoxalines; N-hydroxysulfosuccinimidyl (sulfo-NHS) ester functionalized dyes; N-hydroxysuccinimidyl (NHS) functionalized dyes; vinyl sulfone dyes (e.g., REMAZOL® line of coal tar dyestuffs, such as REMAZOL® Blue, produced by DyStar Textilfarben GmbH & Co. Deutschland KG; and Reactive Black 5); and sulfonyl chloride dyes (e.g., lissamine rhodamine, and dabsyl chloride); tetrafluorophenyl ester functionalized dyes; isothiocyanate functionalized dyes; and iodoacetyl functionalized dyes. The invention also encompasses dyes that are structurally equivalent to the dyes listed herein.

The structure of Erioglaucine (also known as FD&C Blue 1, Acid Blue 9, Brilliant Blue FCF, or N-ethyl-N-[4-[[4-[ethyl[(3-sulfophenyl)methyl]amino]phenyl](2-sulfophenyl)methylene]-2,5-cyclohexadien-1-ylidene]-3-sulfo-, inner salt, disodium salt, CAS number [3844-45-9]) is:

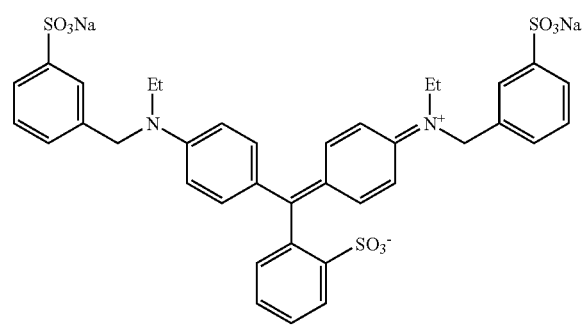

A sulfonyl chloride form of this dye may be prepared via methods known to those skilled in the art. The chemical structures of two possible isomers of the sulfonyl chloride of Erioglaucine are:

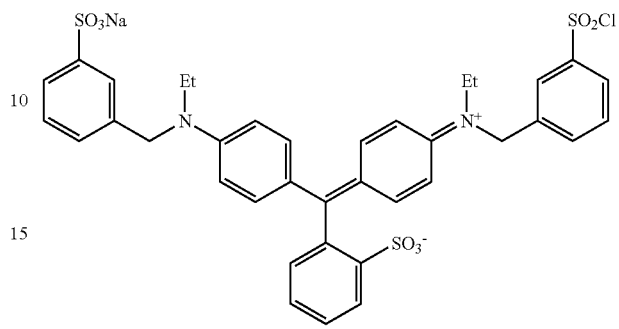

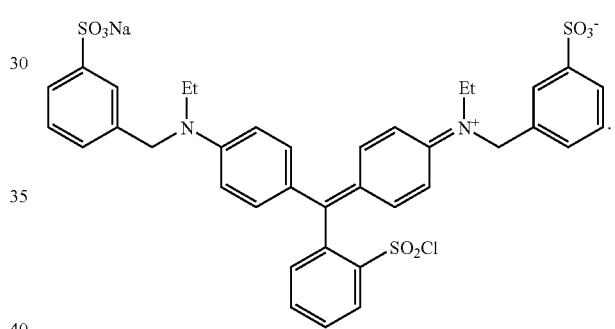

The names of these dyes are N-ethyl-N-[4-[[4-[ethyl[(3-(chlorosulfonyl)phenyl)methyl]amino]phenyl](2-sulfophenyl)methylene]-2,5-cyclohexadien-1-ylidene]-3-sulfo-, inner salt, sodium salt and N-ethyl-N-[4-[[4-ethyl[(3-sulfophenyl)methyl]amino]phenyl](2-(chlorosulfonyl)phenyl) methylene]-2,5-cyclohexadien-1-ylidene]-3-sulfo-, inner salt, sodium salt.

Sulfonyl chlorides are known to react preferentially with primary amine groups, such as those found on lysine groups or on the N-terminus of peptides and proteins. Thus, the dyes shown above may be used directly to label peptides. Alternatively, via methods known to those in the art, the sulfonyl chloride form of Erioglaucine may be further chemically modified to present other functional groups, such as NHS esters, iodosuccinimides or other reactive groups. Examples of such chemical modifications of other dyes are given in U.S. Pat. No. 5,393,514, U.S. Pat. No. 5,846,737 and U.S. Pat. No. 5,798,276, the entire teachings of which are all incorporated herein by reference.

Fiber reactive dyes are based on chlorine or fluorine leaving group chemistries and are known as chloro- or fluorotriazinyl dyes. Reactive Dyes range from very low reactivity to highly reactive (such as CIBRACRON™ F and PROCION® MX) under a variety of temperature ranges. The reactive group is a triazinyl ring (a six-sided ring with three nitrogens). The reaction is considered a nucleophilic bimolecular substitution mechanism. It is a specific base-catalyzed addition of the nucleophilic functional group of the substrate to the electrophilic center of the reactive group of the dye. Reactive Blue 4 and Reactive Yellow 86 have the following structure:

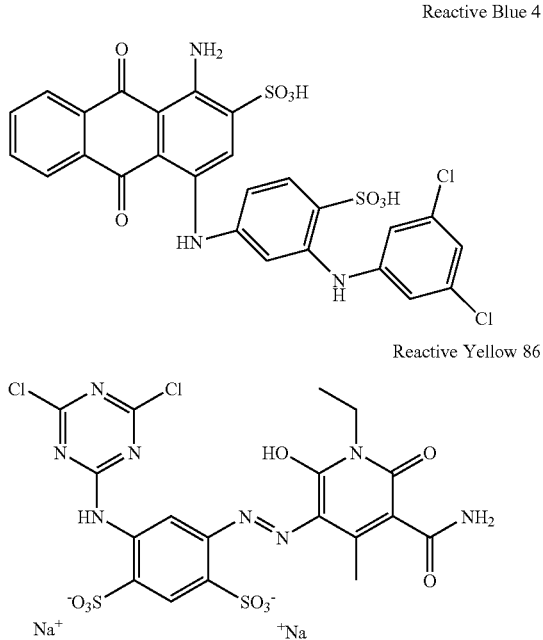

Reactive Blue 4

Reactive Yellow 86

Figure 2:
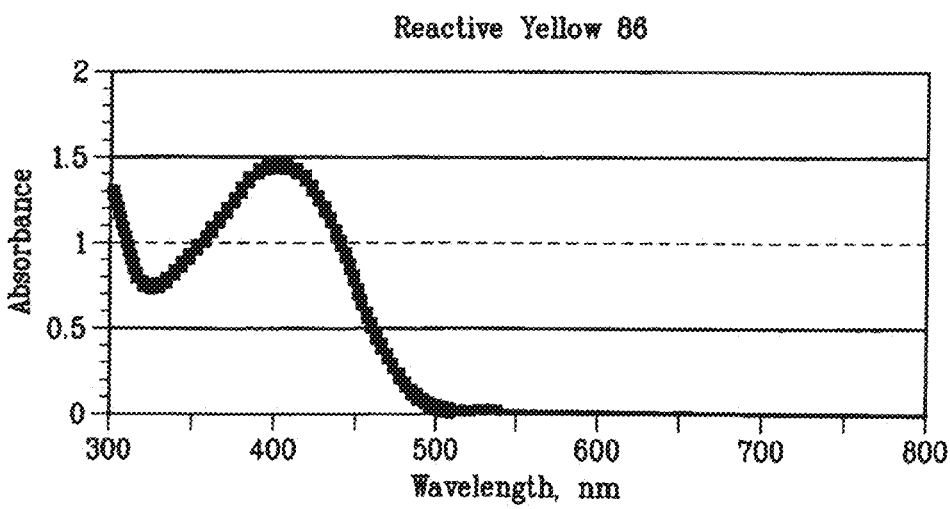
FIG. 2 illustrates the spectra of Reactive Yellow 86 in water.

The UV/Visible spectra in water of triazine dye Reactive Blue 4 is illustrated in FIG. 1, while the spectra of triazine dye Reactive Yellow 86 is illustrated in FIG. 2.

Vinyl sulfone dyes react via a nucleophilic addition mechanism, where there is frequently an elimination step before the addition step, resulting in the formation of a vinylic intermediate. Typically, there is a base-catalyzed elimination of a nucleofugic leaving group followed by a base-catalyzed addition of a nucleophilic functional group of the substrate. REMAZOL® dyes are examples of vinyl sulfone dyes utilizing the reactive group: —SO$_2$—CH$_2$—CH$_2$—OSO$_3$Na. Reactive Blue 19 and Reactive Black 5 have the following structures:

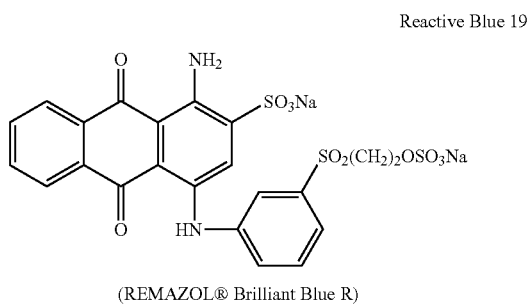

Reactive Blue 19

(REMAZOL® Brilliant Blue R)

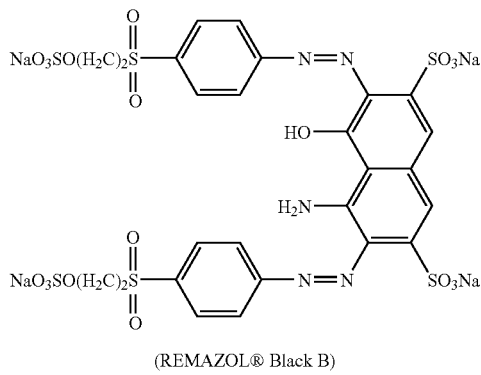

Reactive Black 5

(REMAZOL® Black B)

Figure 3:
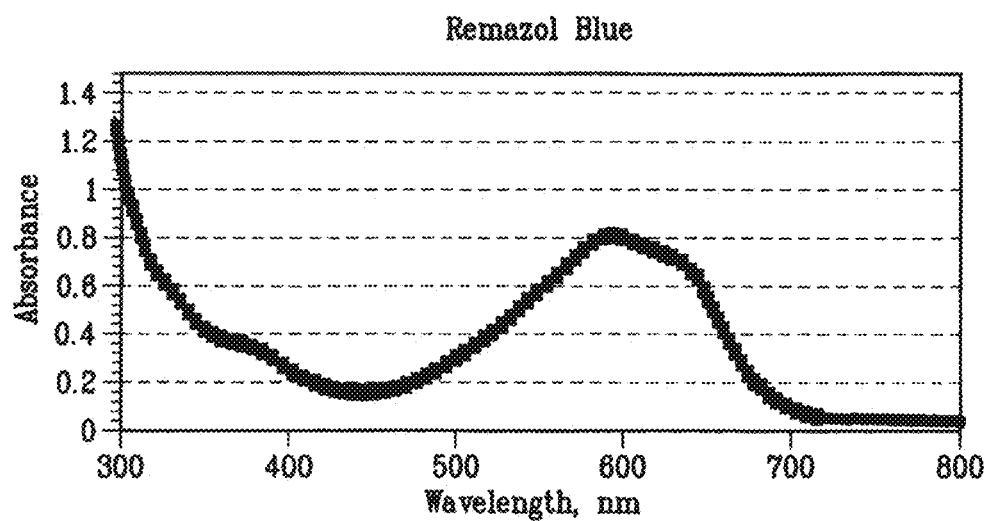
FIG. 3 illustrates the spectra of REMAZOL® Brilliant Blue R in water.
Figure 4:
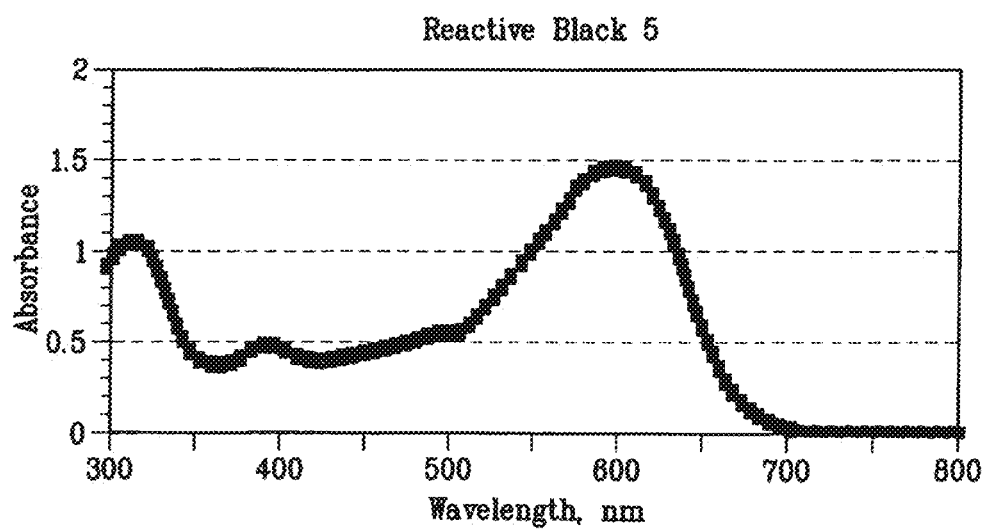
FIG. 4 illustrates the spectra of Reactive Black 5 in water.

The UV/Visible spectra in water of REMAZOL® Brilliant Blue R is illustrated in FIG. 3, while the spectra of REMAZOL® Black B vinyl sulfone is illustrated in FIG. 4.

Sulfonyl chlorides are reactive sulfonic acid derivatives. Reaction of sulfonyl chloride compounds with a primary amine-containing molecule proceeds with the loss of chlorine and the formation of a sulfonamide linkage. The structure of the sulfonyl chloride dye, lissamine rhodamine B sulfonyl chloride (i.e., Xanthylium, 9-[4-(chlorosulfonyl)-2-sulfophenyl]-3,6-bis(diethylamino)-, inner salt, available from Molecular Probes, Inc., Eugene, Oreg., CAS Number/Name: 62796-29-6), is:

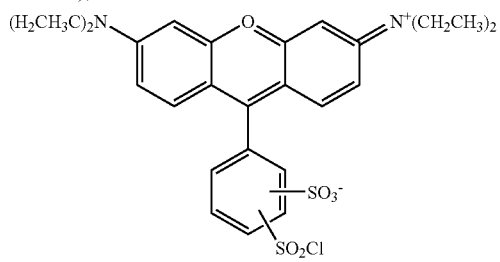

Lissamine Rhodamine B Sulfonyl Chloride

N-hydroxysulfosuccinimidyl (sulfo-NHS) ester functionalized dyes are water-soluble and react with primary amine-containing molecules to form an amide bond with the loss of the sulfo-NHS group. N-hydroxysuccinimidyl (NHS) functionalized dyes are also reactive to amine groups. The structure of the dye functionalized with NHS ester, BODIPY® FL, SSE (i.e., 4,4-difluoro-5,7-dimethyl-4-bora-3a,4a-diaza-s-indacene-3-propionic acid, sulfosuccinimidyl ester, sodium salt; available from Molecular Probes, Eugene, Oreg.), is:

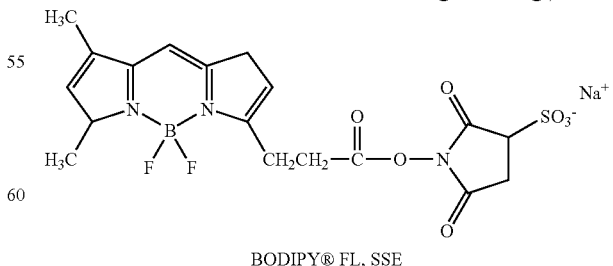

BODIPY® FL, SSE

The colorimetric component(s) is attached to the substrate by methods known in the art, such as those described by Greg Hermanson in BIOCONJUGATE TECHNIQUES (1996), available from Academic Press, San Diego, Calif., the teachings of which are incorporated herein in their entirety by reference. In some embodiments, the colorimetric components are covalently attached to the peptide. For example, a protective group can be used to block one of the attachment sites on a peptide chain while a first colorimetric component is attached (e.g., a triazine dye attached to a serine group or a vinyl sulfone dye attached to a, cysteine group). After the first colorimetric component is attached, the protecting group is removed in order to attach a second calorimetric component. Surfactants, such as Triton-X, can be used to promote the attachment of the colorimetric components to the peptide chains and/or improve solubility.

The extent to which the substrate is labeled with colorimetric components will vary and can depend on many factors such as, for example, the needs of the application in which the substrate is to be used, manufacturing requirements, and the desires of the practitioner of this invention. One method of characterizing the level, or amount, of labeling a substrate includes is to refer to its "dye-to-substrate ratio." As used herein, the term "dye-to-substrate" ratio is the molar ratio of the molar concentration of dye to the molar concentration of substrate and is a means of characterizing the level of labeling of the substrate as well as the efficiency of the labeling reaction. For example, a dye-to-substrate ratio of 1.0 would signify that, on average, each substrate is labeled with one colorimetric component. A low dye-to-substrate ratio can signify an incomplete labeling of the substrate (i.e., many peptides have no dye attached to them). In some embodiments, the range of the dye-to-substrate ratio depends on the number of amino acids on the peptide that are to be labeled with the color component. For example, if two sites are to be labeled, then a complete labeling reaction would render a dye-to-substrate ratio of about 2. Suitable dye-to-substrate ratios depend on the exact application. For example, the dye-to-substrate ratio can affect the clarity of the signal, attachment of the substrate to a solid support, and other aspects to the biosensor that can be varied depending on the needs of the practitioner of the invention.

A suitable dye-to-substrate ratio can be determined through experimentation. For example, the peptide of the substrate can be synthesized to add or subtract extra amino acid groups that are suitable targets for attaching the colorimetric components. In this manner, the dye-to-substrate ratio can be varied, and the resulting substrates can be tested to determine what ratio produces acceptable results for a given application. For example, CPI4 contains two cysteine groups at one end that are good targets for vinyl sulfone dyes. This allows for the attachment of two calorimetric components on each peptide. By adding a second colorimetric component, the resulting signal produced by the substrate will be brighter (i.e., having a larger color intensity and/or sharper contrast) than if only one colorimetric component was attached to the substrate. This brighter color may be more favorable for a given application. For example, a dark blue dye may easily be seen on a solid support, but a yellow dye may require more dyes per peptide to create the desired level of color. However, too many dyes on one end of the peptide may create a steric hindrance if, or when, the peptide is attached to a solid support, so there is an optimum dye-to-substrate ratio or ratio range for each substrate and/or application.

Solid Supports

In some embodiments, the substrate is attached to a solid support. Examples of suitable solid supports include a wound dressing (e.g., a bandage or gauze), any material that needs to be sterile or free of microbial contamination, an article that contains or collects the sample (e.g., a urine collection bag, a blood collection bag, a plasma collection bag, a test tube, a body fluid collection tube, a test tube, a catheter, a swab, a swab carrier, a dipstick, or a well of a microplate), a polymer, a membrane, a resin, glass, a sponge, a rigid probe or capillary, a point of care ruler, a disk, a scope, a filter, a lens, foam, cloth, paper, a wipe, a suture, and a bag. In some embodiments of the invention, the solid support is made from materials suitable for sterilization. Examples of suitable methods of sterilizing the solid support include gamma irradiation treatments and ethylene oxide treatments. In some embodiments, the solid support includes a colorimetric component and/or the solid support is made of a colored material.

In preferred embodiments, the solid support is a medical product that contacts a patient or body tissue or fluid samples from a medical patient. For example, in some embodiments, the solid support is a medical device or product having a sample port that allows access to fluid sample (e.g., body or wound fluid), a wicking agent to draw the fluid into the device or product, an assay chamber in which the detection takes place, and a viewing port that allows a practitioner to see the signal that indicates the presence of a microorganism. In further examples, the solid support is a material used to clean the surface of a wound, measure the distance to closure of a wound, obtain samples from a wound, and/or transfer specimens to a clinical microbiology facility. Such solid supports provide a diagnostic or point-of-care (POC) device that could be used by health care providers to quantify and qualify the presence of any infectious or pathogenic microorganisms within a wound. For example, such embodiments could be used to determine if a wound had $10^5$ CFU per ml wound pathogens (or greater). $10^5$ CFU per ml wound pathogens is consider to be critical colonization that indicates a chronic wound is infected.

Figure 5:
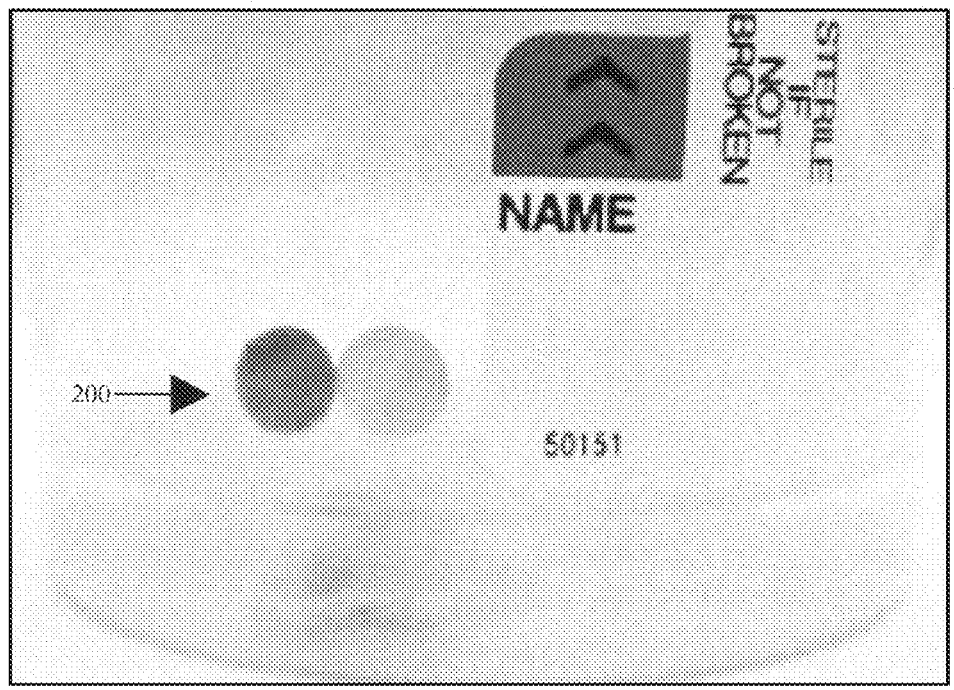
FIG. 5 illustrates a photograph of a lab specimen collection container that includes a sensor of the present invention.

FIG. 5 illustrates a photograph of a lab specimen collection container. The blue color of sensor 500 indicates the presence of one or more specific types of microorganisms in the lab specimen container. Similarly, a sensor could be placed in a swab sample container to indicate the presence of microorganisms in a sample that has been placed into the container.

In some embodiment, sensors containing specific markers for wound pathogens are bound to a collar that is placed at the back of an alginate or a swab (e.g., a cotton or polyurethane swab). The swab draws the fluid from the wound up along the outside of the stem. The fluid then passes from the top of the swab to the collar sensor, and if the microbial proteins of interest are present in the fluid, a signal is produced by the sensor (e.g., a color change). In the case of a simple color dye labeled peptide, the free diffusing color is collected into a membrane that preferentially binds the dye leaving group with a strong affinity. In the case of a zymogen-peptide conjugate, the hydrolysis of the peptide leads to either the activation of the zymogen or the movement of the zymogen into an area that is clearly visible thereby producing an amplification of the color signal.

Figure 6:
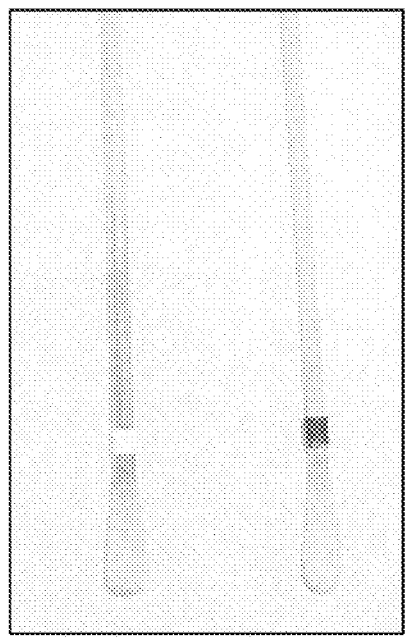
FIG. 6 illustrates a photograph of two swabs that include sensors of the present invention.

FIG. 6 illustrates a photograph of two swabs. The swab on the left has not been exposed to a fluid sample, while the one on the right has been exposed. The sensor attached to the swab on the right has changed color, indicating the presence of *Staphylococcus aureus* in the sample.

Figure 7:
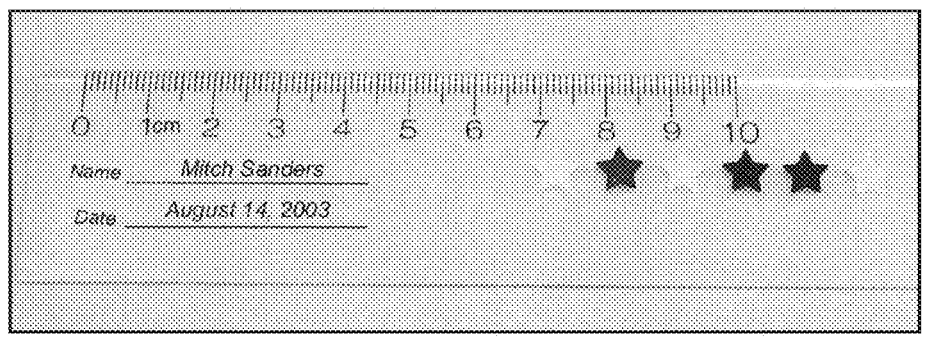
FIG. 7 illustrates a photograph of a ruler that includes sensors of the present invention.
Figure 8:
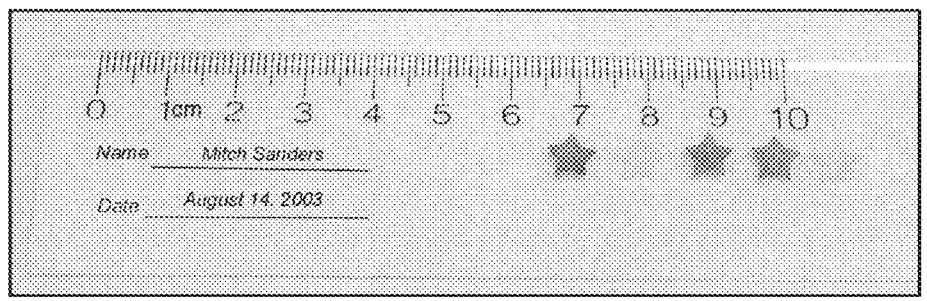
FIG. 8 illustrates the ruler shown in FIG. 7 after exposure to wound fluid that contained proteins from a microorganism specific to the sensors.

In another embodiment, sensors are incorporated onto or into a thin, flexible, and clear plastic ruler that has the dual purpose of measuring the distance of the wound bed and detecting the presence of specific types of microorganisms to determine if a patient will have an incipient infection. In some embodiments, the ruler includes channels positioned in the middle along with one or more color charts that can provide a positive and/or negative control color, an infection sensor or sensors that produce a visible signal in the presence of harmful microorganisms, and/or an area with lines to write patient information (e.g., the patient's identification number, date, and/or time of visit). Optionally, the ruler can comprise specific sensors for one or more species of wound pathogens and/or a broad spectrum sensor that detects a plurality of pathogens. In use, the ruler/sensor combination could be photographed to provide the caregiver with a permanent record for the patient's chart. FIG. 7 illustrates a photograph of such a ruler. FIG. 8 illustrates the ruler after exposure to wound fluid that contained proteins from a microorganism specific to the sensors and the sensors have undergone a change in color, thereby indicating the presence of microorganisms.

In another embodiment, sensors are included on a wound cleansing wipe or sponge that could be used, for example, to clean a wound and detect the presence of microorganisms. The sponge or wipe comprises an absorbent material such as cloth, paper, cotton, sponge, or non-woven fibrous material. A sensor would be attached or incorporated on the wipe or sponge in a pattern that would provide uniform coverage for detecting the proteins from an infected wound. In some embodiments, the sensors are printed on the material in a pattern, such as waves, mesh, grid, or spots. Preferably, the signal produced by the substrate is easily identifiable from the typical colors of wound fluid. In some embodiments, the wipe or sponge is also used to spread a therapeutic or antibiotic substance.

Figure 9:
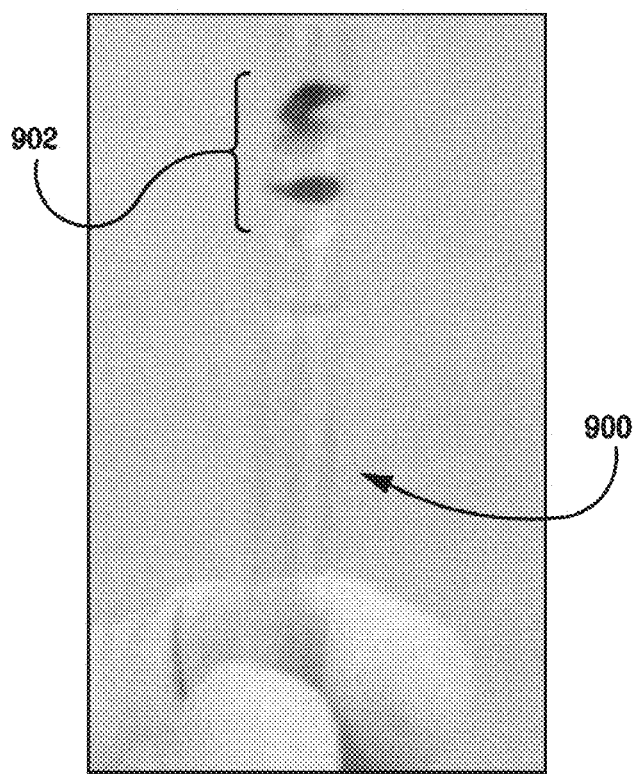
FIG. 9 illustrates a rigid capillary probe that includes sensors of the present invention.
Figure 10:
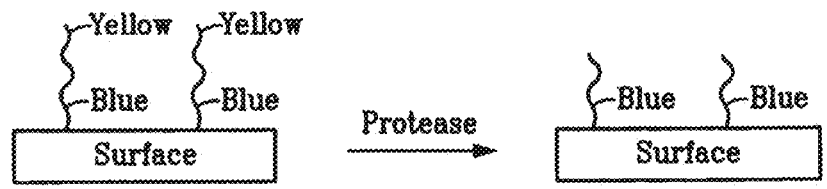
FIG. 10 illustrates an embodiment where a substrate includes two dissimilar colorimetric components.

In yet another embodiment, the sensors are placed at the tip of a cylindrical rigid probe or capillary used to sample wound fluid. The probe is rigid enough to put pressure on the wound to express and draw up fluid into a hollow chamber that contains the sensors. In some embodiments, the probe includes a broad spectrum of sensors, a series of specific sensors, or both. In some embodiments, the chambers are made of soft or hard clear materials (such as glass, silicone, or other materials with similar properties). The inner chamber of the probe draws up the liquid by capillary action and also contains membrane filters that include calorimetric sensors that are specific to each microorganism or pathogen of interest and/or form a sensor that can detect a broad spectrum of microorganisms. Optionally, the probe or capillary includes an absorbent wick comprising polyurethane or other suitable material that is used to draw the sample fluid into the membrane sensor regions. FIG. 9 illustrates a rigid capillary probe 900 that includes the sensors 902.

In another embodiment, the sensors are incorporated into a fine strip, thin film, mesh, or suture material that is placed on wound to collect fluid. In some embodiments, the sensors produce a signal within minutes of detecting the presence of a microorganism(s) of interest. In some embodiments, the strips, film, mesh, or sutures are made of a non-absorbent material (e.g., nylon or polyethylene fibers). In other embodiments, the strips, film, mesh, or sutures are made from an absorbent material (e.g., polyurethane). In use, the thin films, mesh, or sutures can be placed in a plastic or glass test tube carrier commonly used to transport swab samples to a laboratory, thereby providing a sensor system for the caregiver and a vessel for a confirmatory readout within a hospital laboratory.

In some embodiments, the point of care (POC) sensor device can be incorporated into a specimen bag or jar that can be used to transfer a sample (e.g., a tissue or biopsy sample) to a lab. In further embodiments, the peptides are implanted onto a thin film and/or directly impregnated onto the sample jar or bag. Optionally, non-ionic detergents (e.g., HECAMEG, TRINTON X100, or TWEEN) and/or other reagent(s) (e.g., buffers, such as PIPES (pKa=6.76), DNAse I, and/or non-porous glass or metal beads) are included in the POC sensor and/or specimen bag or jar in order to control the optimal activity of the sensors, to hydrolyze the DNA from the tissue sample and prevent it from becoming too viscous, to macerate the tissue by gentle swirling, to permeablize the tissue sample to promote detection of any microorganism of interest, and/or to improve the homogeneity of the biopsy/tissue sample.

In some embodiments, the POC device is a disposable item that would be used once and then placed in biohazard waste. Upon autoclaving the device would be destroyed and the patient's information would be kept confidential.

In some embodiments, the substrate is adhered, attached, coupled, or bound to the solid support. Methods for doing so are known in the art. For example, the substrate can be attached to the solid support through noncovalent interactions (e.g., hydrophobic interactions, hydrophilic interaction, electrostatic interactions, or through a sorption process) or by covalent binding. In further embodiments, the substrate includes hydrophobic leaving groups and is non-covalently bound to a hydrophobic surface of a solid support. In other embodiments, hydrophilic or hydrophobic substrates are coupled to surfaces by disulfide or primary amines, thiol groups, carboxyl groups, hydroxyl groups, or with the use of crosslinkers (e.g., sulfo EMCS (N-Maleimidocaproyloxy sulfoxuccinimide ester), available from Pierce Biotechnology, Inc., Rockford, Ill.). In yet another embodiment, the substrate is coupled to a solid support using non-essential reactive termini such as free amines, carboxylic acids, or thiol groups that do not effect the substrate's interaction with a protein produced by a microorganism. Free amines can be coupled to carboxyl groups on the substrate using, for example, a 10-fold molar excess of either N-ethyl-N'-(3-dimethylaminopropyl)carbodiimide hydrochloride or N-cyclohexyl-N'-2-(4'-methyl-morpholinium)ethyl carbodiimide-p-toluene sulphonate for ~2 hrs at ~4° C. in distilled water, adjusted to a pH ~4.5, to stimulate the condensation reaction to form a peptide linkage. Thiol groups can be reduced with Dithiothreitol or Tris (2-Carboxyethyl)Phosphine and then coupled to a free amino group on a surface with N-e-Male-imidocaproic acid (see D. G. Griffith et al., *N-Polymethylen-ecarboxymaleimides: A new class of probes for membrane sulfhydryl groups,* 134 FEBS LETT. 261-63 (1981), which is incorporated herein by reference). In another embodiment, the substrate is attached to the solid support by attractive interactions between the amino acids of the peptide and the solid support. For example, a peptide with consecutive histidine residues can be bound to a resin (e.g., SEPHAROSE®) containing nickel ions immobilized by covalently attached NTA. In yet another example, the solid support has a polar charge (e.g., a negatively charged membrane) and at least some portion of the substrate (e.g., one or more peptides of the substrate's peptide chain) has a polar charge opposite of that on the solid support. These opposite charges provide for the attachment of the substrate to the solid support.

In some embodiments, substrate modification comprises cleaving at least a portion of the substrate, wherein the portion includes one of the colorimetric components and the cleaving results in a visible color change. For example, if the substrate includes both blue and yellow colorimetric components, the uncleaved substrate can appear green. After a protein cleaves a portion of the substrate that includes the yellow colorimetric component, the cleaved portion is removed from the immediate presence of the uncleaved portion, leaving the uncleaved portion to appear blue. The visible color change indicates the presence of the microorganism in the sample, while absence of a color change indicates the absence of the microorganism.

FIG. 5 illustrates a schematic of one embodiment of the invention. The unmodified substrates comprise a peptide, a yellow calorimetric component, and a blue calorimetric component. The unmodified substrate has a green hue. After modification by a protease, a portion of the peptide that includes the yellow calorimetric component is cleaved, leaving the substrate with only a blue colorimetric component. Hence, the modification of the substrate produces a signal in the form of a color change of green to blue.

In some embodiments, the modification of the substrate includes cleaving one peptide bond of the peptide. In other embodiments, the modification of the substrate includes cleaving at least one calorimetric compound from the peptide, resulting in a visible color change. In a further embodiment, the modification of the substrate includes hydrolyzing at least one peptide bond in the peptide and results in at least a portion of the peptide being cleaved from the substrate. The cleaved portion includes at least one of the calorimetric components, resulting in a visible color change.

The exact mechanisms employed to remove the cleaved portion of the substrate from the immediate presence of the uncleaved portion can vary. For example, the cleaved portion can diffuse, sorb, and/or migrate into the surrounding environment (e.g., such as a wound dressing) or it can be washed away with a liquid.

Collector

In some embodiments, a collector is used to remove the cleaved portions so that the signal is detectable. As used herein, a "collector" is a solid or surface comprising a property that attracts the cleaved portion of a substrate. In these embodiments, one or more of the cleaved portions can have a higher attraction or affinity for the collector than for the other portion of the substrate and/or the solid support so that the cleaved portions migrate, sorb, and/or diffuse from the substrate and towards the collector or some point remote from the noncleaved portion of the substrate or the modified substrate. In some embodiments, the distance that the cleaved portion migrates is sufficient so that a detectable signal results. In some embodiments, the migration of the cleaved portion(s) results in a detectable signal.

In some embodiments, the cleaved portion of the substrate can be captured on a collector. In further embodiments, the cleaved portion is captured on a colored collector. In still further embodiments, modification of the substrate results in a cleaved portion being captured on the surface of a colored collector, thereby producing or indicating a change in color of the solid support. That is, once the cleaved portion of the substrate is released, it is attracted to the collector by one or more forces (e.g., a force caused by an electrostatic or magnetic charge, or a chemical binding). In another embodiment, the collector causes the cleaved portion to migrate a sufficient distance from the substrate so that the color of the solid support is detectable.

As a nonlimiting example, a substrate can include a first colorimetric component (e.g., a yellow colorimetric component attached to a peptide). Modification can include cleaving the substrate such that a first cleaved peptide portion includes the first colorimetric component and a second cleaved peptide portion does not include a colorimetric component. The first cleaved peptide portion can be attracted towards the collector, resulting in a visible color change of the collector (e.g., the collector can appear more yellow). If the substrate was originally attached to a solid support, the combination of the solid support and uncleaved portion of the substrate can exhibit a change in color (e.g., appearing less yellow or becoming colorless).

In another nonlimiting example, the first and second cleaved portion can be present in a liquid and the migration of the first portion that includes the colorimetric component (e.g., yellow) towards a collector can result in the liquid exhibiting a change in color (e.g., appearing less yellow or becoming colorless).

In yet another nonlimiting example, the unmodified substrate can include at least two calorimetric components (e.g., a yellow and a blue colorimetric component) and the modification can result in the first cleaved portion including the yellow calorimetric component and the second portion including the blue colorimetric component. Prior to substantial migration of the first calorimetric component, the close proximity of the first and second calorimetric components can provide a green appearance. As the first portion migrates towards a collector, the individual colors become more apparent. For example, if the second portion is attached to a solid support, the combination of the solid support and the second portion can change color (e.g., becoming more blue in hue) as the first portion migrates towards a collector and away from the solid support and the second portion. If, for example, the original substrate was included in a liquid, the liquid will continue to appear green immediately after the modification. However, as the first cleaved portion migrates towards the collector, the remaining combination of fluid and second cleaved portion can change color (e.g., becoming more blue in hue). Optionally or additionally, the modification of the substrate can result in the collector producing a color change (e.g., the collector exhibiting a more yellow color as the yellow first cleaved portion collects onto the surface of the collector).

In some embodiments, the modification results in a visible color change in a predetermined pattern. For example, the modification can result in the appearance, disappearance, and/or color change of a shape (e.g., a symbol, letter, or word). This can be accomplished with, for example, attaching substrates onto a solid support in a pattern (e.g., a star, cross, or plus sign). For example, the solid support material can be blue and the substrates with yellow colorimetric components can be arranged on the solid support in the shape of a star. Prior to modification, the solid support appears to have a blue background with a green star (with the green hue of the star arising from the mixture of the yellow hue of the substrate and the blue hue of the solid support). Modification results in the cleavage of the yellow colorimetric components from the substrate and is indicated by the fading of the green star, leaving the solid support to appear blue. In another embodiment, a collector is employed and the collect is formed in such a way that cleaved portions will be attracted to a predetermined area of the collector. For example, the substrates can include a yellow colorimetric component and the collector can comprise a blue material. Modification of the substrate results in the yellow colorimetric components collecting on the collector in a predetermined shape, such as the shape of a cross. In this manner, modification of the substrates is indicated by the appearance of a cross with a green appearance (due to the combined blue hue of the collector and the yellow of the colorimetric components). In yet another embodiment, modification of the substrate results in the appearance, disappearance, and/or visible change of color in one or more predetermined shape on both a solid support and a collector. Optionally, many different types of substrates, collector surfaces, and solid support surfaces are used so that a plurality of modification and/or microorganisms can be detected. This invention encompasses the use of more than one shape, combination of shapes, and color shifts on one or more collectors and/or solid supports which will be apparent to one skilled in the art.

The examples described herein are not meant to be limiting in any way, and other combinations of solid support(s), type and number of colorimetric components, and migration-inducing attractive and/or repulsive collectors are also encompassed by this invention.

In one embodiment, the invention includes a method of detecting the modification of a substrate, wherein an unmodified substrate comprises a peptide with at least one colorimetric component, wherein the method comprises the steps of a) exposing the substrate to a sample under conditions that will result in the modification of the substrate, wherein the modification of the substrate comprises cleaving at least a portion of the peptide that includes at least one colorimetric component and the cleaved portion migrates toward a collector, wherein the migration results in a visible color change; and b) detecting the presence or absence of the visible color change, wherein a visible color change indicates the modification of the substrate and the absence of a visible color change indicates an absence of the modification of the substrate.

Figure 11:
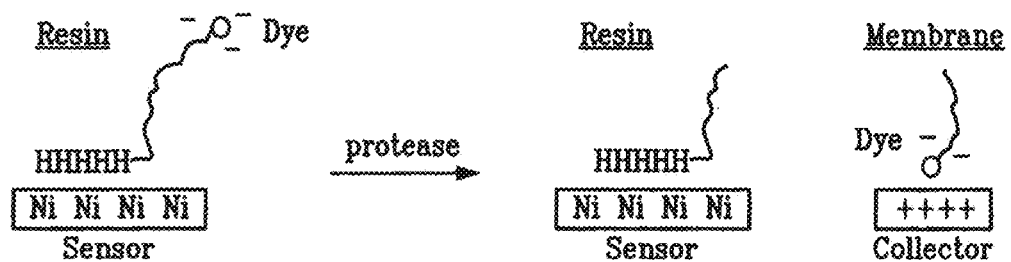
FIG. 11 illustrates a schematic of an embodiment of the invention where a nickel resin is attached to a peptide that includes a colorimetric component.

FIG. 11 illustrates a schematic of a metal chelation embodiment of the invention. A colorimetric component, in this case a dye, is included on a peptide that is attached to a nickel resin solid support. A protease cleaves a portion of the peptide, and the cleaved portion has a greater affinity for a membrane collector than for the original surface. As the dye migrates towards the collector, the remaining peptide and solid support produce a visible color change. Optionally, the collector produces a signal as the dye migrates toward or onto the collector.

Figure 12:
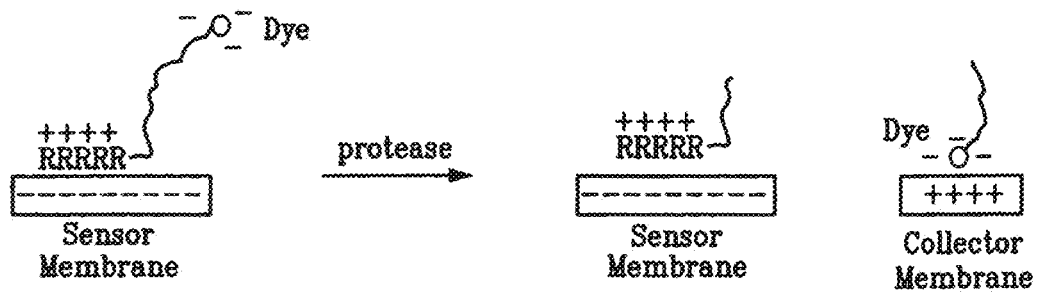
FIG. 12 illustrates a schematic of an embodiment of the invention where a charged membrane is attached to peptide that includes a colorimetric component.

FIG. 12 illustrates an embodiment of the invention where a charged membrane is coupled to substrate that includes a colorimetric component. A protease cleaves a portion of the peptide, and the cleaved portion has a greater affinity for the membrane collector than for the original surface. As the dye migrates towards the collector, the remaining substrate and solid support produce a visible color change. Optionally, the collector produces a signal as the dye migrates toward it.

The collectors can be made of any suitable material that facilitates the migration of cleaved portions of the substrate. For example, the collector can include a membrane, a resin, a polymer, a film, glass, or a chelating material. In some embodiments, the collector is attached to a solid surface, such as a wound dressing (e.g., a bandage or gauze), any material that needs to be sterile or free of microbial contamination, an article that contains or collects the sample (e.g., a urine collection bag, a blood collection bag, a plasma collection bag, a test tube, a body fluid collection tube, a test tube, a catheter, a swab, a dipstick, or a well of a microplate), a polymer, a membrane, a resin, glass, a sponge, a disk, a scope, a filter, a lens, foam, cloth, paper, a suture, and a bag. In some embodiments of the invention, the solid support is made from materials suitable for sterilization. Examples of suitable methods of sterilizing the collector include gamma irradiation treatments. In some embodiments, the collector includes a calorimetric component or is made of a colored material.

As part of their normal growth processes, many microorganisms secrete, or cause to be secreted, a number of proteins into their growth environment, such as enzymes. These proteins have numerous functions including, but not limited to, the release of nutrients, protection against host defenses, cell envelope synthesis (in bacteria) and/or maintenance, and others as yet undetermined. Many microorganisms also produce proteins on their cell surface that are exposed to (and interact with) the extracellular environment. Many of these proteins are specific to the microorganism that secretes them, and as such, can serve as specific markers for the presence of those microorganisms. This invention includes a method and/or system that can detect the presence of these produced and/or secreted proteins and can equally serve to indicate the presence of the producing/secreting microorganism. Alternatively, this invention provides for a method and/or system that can detect the absence of these produced and/or secreted, proteins so as to indicate the absence of the producing/secreting microorganism. Such a detection method and/or system are useful for detecting or diagnosing the presence of a microorganism and/or an infection (e.g., a wound infection).

In some embodiments, a microorganism produces the protein that modifies the substrate. This invention includes methods for detecting the presence or absence of a microorganism in a sample. For example, the method can comprise the steps of a) contacting the sample with a substrate under conditions that will result in a modification of the substrate by the microorganism and b) detecting the modification or an absence of the modification. A protein produced, secreted, or expressed by the microorganism modifies the substrate. In some embodiments, the modification comprises cleaving at least a portion of the substrate, wherein the portion includes one of the calorimetric components and the cleaving results in a visible color change, thus indicating the presence of the microorganism in the sample, and absence of the modification indicates the absence of the microorganism.

A microorganism detection system, as described herein, can be tailored to detect one specific microorganism by identifying a protein, such as a secreted enzyme, specific to the microorganism to be detected. Alternatively, a system can be designed to simultaneously identify more than one microorganism species (for example, at least 2, at least 5, or at least 10 different microorganism species), such as those that commonly infect wounds. Preferably, this goal is achieved by identifying those proteins that are common to certain classes of pathogenic microorganisms, but which are not common to non-pathogenic microorganisms. Such proteins can be identified, for example, with a computer based bioinformatics screen of the microbial genomic databases.

The presence of a microorganism can be detected by designing a synthetic substrate that will specifically react with a protein that is present on the surface of the cell or is secreted into the microorganism's growth environment. These synthetic substrates can be labeled with a detectable label such that under conditions wherein their respective proteins specifically react with them, the substrates undergo a modification that is indicated by the detectable label. For example, the detectable label can produce a visible color change.

Examples of microorganisms that can be detected by the various embodiments of this invention include bacteria, viruses, and fungi. Preferably, the microorganism is a bacteria. Examples of bacteria include, but are not limited to *staphylococcus* (for example, *Staphylococcus aureus, Staphylococcus epidermidis,* or *Staphylococcus saprophyticus*), *streptococcus* (for example, *Streptococcus pyogenes, Streptococcus pneumoniae,* or *Streptococcus agalactiae*), *enterococcus* (for example, *Enterococcus faecalis* or *Enterococcus faecium*), *corynebacteria* species (for example, *Corynebacterium diptheriae*), *bacillus* (for example, *Bacillus anthracis*), *listeria* (for example, *Listeria monocytogenes*), *clostridium* species (for example, *Clostridium perfringens, Clostridium tetanus, Clostridium botulinum, Clostridium difficile*), *Neisseria* species (for example, *Neisseria meningitidis* or *Neisseria gonorrhoeae*), *E. coli, shigella* species, *salmo-* nella species, yersinia species (for example, *Yersinia pestis, Yersinia pseudotuberculosis,* or *Yersinia enterocolitica*), *Vibrio cholerae, Campylobacter* species (for example, *Campylobacter jejuni* or *Campylobacter fetus*), *Helicobacter pylori,* pseudomonas (for example, *Pseudomonas aeruginosa* or *Pseudomonas mallei*), *Haemophilus influenzae, Bordetella pertussis, Mycoplasina pneumoniae, Ureaplasma urealyticum, Legionella pneumophila, Treponema pallidum, Leptospira interrogans, Borrelia burgdorferi,* mycobacteria (for example, *Mycobacterium tuberculosis* or *Mycobacterium leprae*), *actinomyces* species, *nocardia* species, *chlamydia* (for example, *Chliamydia psittaci, Chlamydia trachomatis,* or *Chlamydia pneumoniae*), *rickettsia* (for example, *Rickettsia ricketsii, Rickettsia prowazekii,* or *Rickettsia akari*), brucella (for example, *Brucella abortus, Brucella melitensis,* or *Brucella suis*), *Proteus mirabilis, Serratia marcescens, Enterobacter clocae, Acetinobacter anitratus, Klebsiella pneumoniae* and *Francisella tularensis.* Preferably, the bacteria are one or more of the group comprising a *staphylococcus,* a *streptococcus,* a *enterococcus,* a *bacillus,* a *clostridium, E. coli, yersinia, pseudomonas, Proteus mirabilis, Serratia marcescens, Enterobacter clocae, Acetinobacter anitratus, Klebsiella pneumoniae,* or *Mycobacterium leprae.* More preferably, the bacteria are one or more of the group comprising *Staphylococcus aureus, Staphylococcus epidermidis, Streptococcus pyogenes, Pseudomonas aeruginosa, Enterococcus faecalis, Proteus mirabilis, Serratia marcescens, Enterobacter clocae, Acetinobacter anitratus, Klebsiella pneumoniae* and/or *Escherichia coli.*

The embodiments of this invention can also be used to detect one or more types of fungi. Preferably the fungi are those most capable of causing property damage and/or those that cause disease in mammals. Examples of fungi include *Absidia, Acremonium, Alternaria, Apophysomyces, Arthroderma, Aspergillus, Aureobasidium, Basidiobolus, Beauveria, Bipolaris, Blastomyces, Botryosphaeria, Candida, Capronia, Conidiobolus, Cladophialophora, Cladosporium, Clavispora, Coccidioides, Cochliobolus, Cokeromyces, Coniothyrium, Cryptococcus, Cunninghamella, Curvularia, Emericella, Epicoccum, Epidermophyton, Exophiala, Exserohilum, Fennellia, Fonsecaea, Fusarium, Gibberella, Helminthosporium, Histoplasma, Hortaea, Hyphopichia, Issatchenkia, Kluyveromyces, Lacazia, Lasiodiplodia, Leptosphaeria, Lewia, Madurella, Microsporum, Mortierella, Mucor, Mycosphaerella, Nectria, Neosartorya, Neotestudina, Ochroconis, Paracoccidioides, Penicillium, Phialophora, Pichia, Plectosphaerella, Pseudallesheria, Pyrenochaeta, Rhizopus, Saccharomyces, Saksenaea, Scedosporium, Setosphaeria, Sporothrix, Stephanoascus, Stachybotrys* (for example, *Stachybotrys chartarum* or *Stachybotrys echinata*), *Syncephalastrum, Trichophyton, Wangliella,* and *Yarrowia.*

These lists of bacteria and fungi comprise only examples of microorganisms to which this invention can be applied, and are not meant to be exhaustive. This invention can be applied to any presently known bacteria and fungus, as well as any species discovered in the future.

In some embodiments, the protein that interacts with the substrate to produce the modification is an enzyme. Since a small amount of enzyme can catalyze the turnover of a substantial amount of substrate, basing a detection system on enzymes provides for sensitive tests. In other embodiments, the proteins are pathogen-specific enzymes. As used herein, a "pathogen-specific enzyme" is an enzyme produced and/or secreted by a pathogenic microorganism, but not produced and/or secreted by a non-pathogenic microorganism.

This invention includes a method for detecting the presence or absence of an enzyme in a sample. In one example, the method comprises the steps of a) contacting the sample with a substrate under conditions that will result in a modification of the substrate by the enzyme and b) detecting the modification or an absence of the modification. In some embodiments, the modification comprises hydrolyzing at least one peptide bond in the peptide and resulting in at least a portion of the peptide being cleaved from the substrate, wherein the portion of the peptide cleaved from the substrate includes one of the calorimetric components and wherein the cleaving results in a visible color change, thus indicating the presence of the enzyme in the sample, and absence of the modification indicates the absence of the enzyme in the sample.

Enzymes can be grouped into classes insofar as they represent targets for developing agents to detect the microorganisms that produce them and present them on the cell surface or secrete them into their growth environment. As described herein, enzymes are grouped into nine classes: a lysin (i.e., an enzyme that functions to lyse host cells), an autolysin, an exotoxin, a matrix binding enzyme, a lipase; a cell wall enzyme (i.e., an enzyme involved in the synthesis and turnover of bacterial cell wall components, including peptidoglycan), a protease (i.e., an enzyme that specifically or nonspecifically cleaves a peptide, polypeptide, or protein), a hydrolase (i.e., an enzyme that breaks down polymeric molecules into their subunits), a metabolic enzyme (i.e., an enzyme designed to perform various housekeeping functions of the cell, such as breaking down nutrients into components that are useful to the cell), or a virulence factor enzyme (i.e., an enzyme that is required by the bacterial cell to cause an infection).

Examples of potential samples on/in which the presence or absence of microorganisms are detected include a wound; a body fluid (e.g., such as blood, urine, sputum, or wound fluid such as pus); a piece of hair; a piece of nail; a piece of shell; a piece of scale; a piece of feather; a piece of tissue (e.g., a medical tissue sample or a portion of meat, fish, or poultry); any article that microorganisms may be contained on/in (e.g., an article implanted in an animal's body, catheter, a urine collection bag, a blood collection bag, a plasma collection bag, a disk, a scope, a filter, a lens, foam, cloth, paper, a suture, a swab, a swab carrier, a dipstick, a sponge, a polymeric article, an article made of a resin, a glass article, a test tube, or a well of a microplate); contact lens solutions; a sponge; a polymeric material; a membrane; an article made of resin or glass; or a swab from an area of a room or building (e.g., an examination room or operating room of a healthcare facility, a bathroom, a kitchen, or a process or manufacturing facility).

In other embodiments, the invention includes a biosensor for detecting the presence or absence of proteins, enzymes, or microorganisms. These biosensors can incorporate methods of the invention as described herein. In one example, the biosensor comprises a solid support and at least one detectably labeled substrate bound to the solid support. In one embodiment, the substrate is covalently bound to the solid support. In another embodiment, the substrate is adhered or attached to the solid support via hydrophobic, hydrophilic, and/or electrostatic interactions between the solid support and the substrate. In yet other embodiments, the substrate is adhered or attached to the solid support through adsorption or absorption. In other embodiments, the substrate includes a peptide and at least two colorimetric components attached to the peptide. The peptide specifically interacts or reacts with the protein of interest. In some embodiments, the colorimetric components are covalently attached to the peptide.

In some embodiments, the biosensor includes at least one substrate that specifically interacts or reacts with the protein, enzyme, or microorganism and at least two colorimetric components covalently attached to the peptide. The interaction or reaction results in the substrate producing a detectable signal to indicate the presence of the protein. In further embodiments, the biosensor detects one or more (e.g., at least ~2, at least ~5, at least ~10, at least ~20, at least ~30, at least ~50, at least ~75, or at least ~100) proteins described herein and produces a signal (e.g., a visible color change) to indicate the presence of the proteins.

In some embodiments, this invention includes a biosensor for detecting the presence of at least two proteins, including a first protein and a second protein. For example, the biosensor of the present invention can include one or more substrates (for example, at least ~2, at least ~5, at least ~10, at least ~20, at least ~30, at least ~50, at least ~75, or at least ~100 substrates) that can interact with one or more produced and/or secreted proteins. In one example, the biosensor comprises a solid support, at least one detectably labeled first substrate, and at least one detectably labeled second substrate. The detectably labeled substrates are attached to the solid support. The first substrate includes a first peptide and at least two colorimetric components attached to the first peptide. The first substrate specifically reacts with the first protein. Similarly, the second substrate includes a second peptide and at least two colorimetric components, and the second substrate specifically reacts with the second protein.

In some embodiments, at least three of the four calorimetric components attached to the first and second substrates are dissimilar. In these multi-colored embodiments, the biosensor can undergo two or more distinct visible color changes to indicate the presence of one or more distinct proteins and/or microorganisms. For example, if one type of substrate is designed to react with one type of protein while a second type of substrate is designed to react with a different protein, and both types of substrate are included on the solid support, a plurality of color changes can be designed to indicate the presence of a plurality of different proteins and/or species of microorganisms.

In one embodiment, the biosensor is for use in a healthcare or home-use setting and is suitable for detecting microorganisms in a wound. In still further embodiments, the biosensor is for use in an agricultural setting. One example of a biosensor in an agricultural setting is a sensor used to detect the presence of microorganisms in food products (e.g., meat, fish, or poultry products).

In some embodiments, the biosensor is contacted directly to an animal body (e.g., a human body). In other embodiments, the biosensor is contacted directly to a wound on an animal body. In those embodiments where the sample is a wound or body fluid, a sterile covering or sterile layer can be used to prevent contamination of the wound or body fluid upon direct contact with the biosensor. In further embodiments, the sterile covering has properties that make it suitable for sterilization, yet the sterile covering does not interfere with the protein/substrate interaction. Examples of suitable methods of sterilizing the biosensor include treatment with gamma irradiation. In another embodiment, the biosensor is viewed through the dressing (e.g., through a clear window in the dressing).

One method of making the biosensor of the present invention is to first determining a specific substrate that can interact with a specific protein characteristic of the microorganism to be detected. The determined specific substrate is labeled with one or more colorimetric components and attached to a solid support. Should the substrate come into contact with the specific protein secreted or expressed by the microorganism of interest, the protein modifies the substrate in a manner that results in the detection of such a modification. For example, as described herein, the modification can produce a visible change in color.

Preferably, the portion of the biosensor that comes into contact with the sample will not adhere excessively to the sample, so as to allow for the easy removal of the biosensor from the sample. For example, if the biosensor comprises a wound dressing, the dressing contacts the wound for a time sufficient for the protein to react with the substrate, and then the dressing is removed from the wound without causing further damage to the wound or surrounding tissue.

The present invention can be used to detect the presence or absence of any pathogen-specific enzyme described herein. For example, the method and/or biosensors can be used to detect the presence or absence of lipase enzymes secreted by pathogenic bacteria. It has been discovered that certain bacteria secrete lipases into their environment as part of their survival and/or virulence mechanisms. The lipases serve to break down lipids in the growth environment in order to release nutrients. Lipases may also play a role in disarming mammalian host defenses during infection. Synthetic substrates for these secreted enzymes can be employed to detect the presence of those pathogenic bacteria that secrete them. By using a substrate comprising at least one synthesized lipid and two or more colorimetric components, it is possible to create substrates that will change color as they are hydrolyzed by secreted lipases. This color change reaction forms the basis of a microbial sensor, which can be incorporated into such items as healthcare products (e.g., wound dressings).

In another example, the invention can be used to detect the presence or absence of a microorganism by detecting the presence or absence of autolytic enzymes associated or produced by a microorganism. Autolysins are enzymes that degrade peptidoglycan, a component of the bacterial cell envelope. Autolytic enzymes serve to break down peptidoglycan, be it that of the parent organism, as part of cell division and turnover functions, or as a means to breakdown cell walls of competing bacteria. When labeled with two or more colorimetric component, a substrate that comprises synthetic peptidoglycan subunits (such as, but not limited to, N-acetyl-β-d-glucosaminide) serves as an indicator that can form the basis of a sensor.

In another example, the methods and/or biosensors of the present invention can be used to detect the presence or absence of beta galactosidase on the surface of the cell of a microorganism (e.g., bacteria). Most bacterial species express beta galactosidase as a cytoplasmic enzyme involved in the metabolism of lactose as an energy source. Certain species of *Streptococcus*, however, display the enzyme on the surface of the cell. A substrate comprising a molecule that acts as a substrate for beta galactosidase and at least two colorimetric components, (including, but not limited to, ortho nitrophenyl β-D-galactopyranoside) could thus be used as a means of detecting microorganisms (e.g., *streptococci*) in the environment.

In some embodiments, this invention features kits for detecting proteins, enzymes, and/or microorganisms. These kits incorporate the methods and biosensors of this invention. In one example, a kit includes a biosensor for detecting the presence or absence of a protein in a sample, and at least one reagent for detecting the substance. In some embodiments, the kits include a collector.

One example of a method for developing an assay for detecting a microorganism that produces at least one protein that is secreted or presented on the surface of the microorganism and a method for using the assay to detect pathogenic bacteria producing the enzyme(s) now follows. This method is not meant to be limiting in any way, as other methods are known in the art.

Step 1) Define an amino acid sequence that uniquely identifies the microorganism of interest. Alternatively an (one or more) amino acid sequence that is unique to a specific group of pathogens, for example, wound-specific pathogens can be determined.

Select an amino acid sequence, for example, a protein, peptide, or polypeptide (marker sequence) that uniquely characterizes or marks the presence of the microorganism or group of microorganisms (for example, wound-specific pathogens) of interest. The selection can be performed utilizing a bioinformatic approach, for example, as described in detail below. One or more amino acid sequences that are unique to a specific microorganism are determined.

Step 2) Obtain sufficient protein to determine conditions facilitating optimal modification of a substrate by the enzyme.

Isolate the protein from the extracellular medium in which the microorganism to be assayed is growing, or from the cell membrane of the microorganism, using standard protein purification techniques, described, for example, in Ausubel (supra).

Alternatively, if the genetic sequence encoding the protein or the location of the genetic sequence encoding the protein are unknown, isolate and clone the genetic sequence encoding the marker amino acid of Step 1, or, first determine the genetic sequence, and then proceed as before.

Step 3) Determine the conditions for growth of the microorganism and for the production of a protein presented on the surface of the cell or secreted by the cell.

Determine medium required for growth of the specific microorganism of interest and for expression of its unique active protein into the medium. Also determine whether a second molecule, for example an enzyme, is required to convert the specific protein from an inactive precursor form to an active form. To determine if the protein has been secreted in an active form, a sample of the microorganism culture is provided with chosen potential substrates and cleavage of these substrates is determined. This can be done, for example, by combining the microorganism that produces the protein with the substrate in the appropriate media and incubating at ~37° C. with gentle shaking. At preset times (e.g., ~0.1, ~0.3, ~1.0, ~3.0, ~5.0, ~24, and ~48 hours) the samples are centrifuged to spin down the microorganism, and a small aliquot is removed for a SDS-PAGE gel sample. After completion of the time course the samples are run on about a 10-15% gradient SDS-PAGE minigel. Then, the proteins are transferred to Immobilon Pseq (Transfer buffer, ~10% CAPS, ~10% methanol pH ~11.0, ~15 V for ~30 minutes) using a Bio-Rad semi-dry transblotting apparatus. Following transfer of the proteins, the blot is stained with Coomassie blue R-250 (~0.25% Coomassie Brilliant Blue R-250, ~50% methanol, ~10% acetic acid) and destained (high destain for ~5 minutes, ~50% methanol, ~10% acetic acid; low destain until complete, ~10% methanol, ~10% acetic acid) followed by sequencing from the N-terminal. Alternatively, the samples can be run on a mass spectrometer in order to map the sites of cleavage.

Optionally, the protein(s) produced by the microorganism(s) in the growth medium are compared with samples taken from clinical samples to ensure that the microorganisms produces the protein in the environment(s) in which they are to be detected. For example, the proteins found in a sample taken from a wound site of a hospital patient can be analyzed and compared with the proteins produced by the microorganism grown in the sample. In this manner, it can be confirmed that the microorganism produces the protein in an actual testing sample or environment and that the protein can form the basis for the detection method.

Step 4) Identify any specific substrate(s) of the active protein. Examples of potential substrates include proteins, peptides, polypeptides, lipids, and peptidoglycan subunits. Label each substrate with a detectable label, for example, a detectable label described herein, or any other detectable label known in the art.

Step 5) Increase the specificity of the protein-substrate interaction (optional) by determining the active or binding site of the protein (for example, using the colorimetric components as described above), then determining the genetic sequence useful for producing the active or binding site, and cloning the determined genetic sequence to generate a more specific substrate.

Step 6) Provide a biosensor comprising one or more of the detectably labeled substrates identified above for detection of the protease of the pathogenic bacteria of interest.

The substrate can be attached to solid support, for example, a wound dressing, or an article that holds the protein and substrate, for example, a body fluid collection tube or bag, a microplate well, or a test tube. The solid support, if desired, can provide a plurality of derivatized binding sites for coupling to the substrate, for example, succimidyl ester labeled primary amine sites on derivatized plates (XENOBIND™ binding plates, available from Xenopore Corp., Hawthorne, N.J.). Optionally, coupling, for example, bovine serum albumin, thereto blocks unoccupied reactive sites on the solid support.

Allow the protein(s) to come into contact with the substrate(s), and monitor the reaction for a modification in the detectably labeled substrate, as described herein. Modification of the substrate indicates that the protein produced and/or secreted by the microorganism is present in the reaction. In addition, the absence of modification of the substrate indicates that the protein is not present in the sample. If the microorganism or protein is from a wound, modification of the substrate indicates that the microorganism is present in the wound, while the absence of modification of the substrate indicates that the particular bacteria is not present in the wound.

EXAMPLES

The present invention will now be illustrated by the following Examples, which are not intended to be limiting in any way.

Example 1

Some Metal Chelation Embodiments

In this example, histidine-tagged peptides were purified based on the ability of consecutive histidine residues to bind to a resin (e.g., SEPHAROSE®) containing nickel ions immobilized by covalently attached NTA.

CPI3, Papa4, and LL3 peptides were labeled on the cysteine site with Reactive Black 5. The SSP3 peptide was labeled on the serine site with Reactive Blue 4. After purification and characterization, the four peptides were bound to NTA resin in phosphate buffered saline (PBS) pH ~7.4 for ~2 hours at about room temperature. The resin was then rinsed extensively with PBS. The NTA resin gave a high level of peptide binding (very dark blue) without non-specific binding, as evidenced by very little binding with non-histidine tagged peptides or free reactive dyes.

The CPI3 and Papa4 peptides on NTA resin were cleaved with *Pseudomonas aeruginosa* (PA14), the SSP3 peptide was cleaved with *Serratia marcescens*, and the LL3 peptide was cleaved with *Streptococcus pyogenes* at ~37° C. The portion of the peptide cleaved off of the surface of the sensor was specifically designed to contain the dye component and was collected on a separate positively charged membrane (membrane SB-6407, available from Pall Corporation, East Hills, N.Y.). The Reactive Black 5 contains negative charges that were attracted to the collector membrane. This interaction created a color change from white to blue on the collector membrane. Control samples consisted of collector membranes added to the resin with no bacteria A strong color difference on the collector membranes was obtained with bacteria when compared to controls. The concept of this experiment is shown in FIG. 11. After exposure to the bacterial, the control membranes remained uncolored or clearly had less coloring than the collector membranes that were exposed to the bacteria.

The CPI3 peptide labeled with Reactive Black 5 was attached to NTA resin and rinsed extensively. The resin was then dried in a filter centrifuge tube and spread onto an adhesive plastic sheet. The resin was soaked in PBS and rinsed extensively to remove loosely bound material. A control and a test sensor were made by then placing a collector membrane (membrane SB-6407, available from Pall Corporation, East Hills, N.Y.) onto the surface. In this manner, a sensor using NTA resin to bind peptide on a surface was obtained. One of the sensors was exposed to *Pseudomonas aeruginosa* (PA14) at ~37° C. and the cleaved peptide with dye was collected onto the collector membrane. The control was exposed to PBS only. The sensor that was exposed to the bacteria expressed a clear color, while the control showed little or no change in color.

Example 2

Some Charged Membrane Embodiments

In this example, a negatively charged membrane (membrane ICE-450, available from Pall Corporation, East Hills, N.Y.) was used to bind peptides that contained a positively charged region placed at the end of the peptide (i.e., the 15 arginines of the peptides). The peptides were labeled with negatively charged dyes which when contained on the cleaved portion of the peptide had low affinity for the negatively charged membrane, but a high affinity for a positively charged collector membrane (membrane SB-6407, available from Pall Corporation, East Hills, N.Y.). This concept is shown in FIG. 12.

The CPI4, Papa5, and T5 peptides were labeled on the cysteine site with Reactive Black 5. After purification and characterization, the three peptides were bound to the negatively charged ICE-450 membrane in phosphate buffered saline (PBS) pH ~7.4 overnight. The membranes were then rinsed with PBS. Next, positively charge membranes (membrane SB-6407, available from Pall Corporation, East Hills, N.Y.) were placed on either side of the peptide bound membrane in PBS to take off any loosely adhered material. The non-specifically bound material was removed by collecting it on the positively charged membrane. The peptide bound membranes were cleaned in this manner until no color is seen to come off of the membranes.

Figure 13:
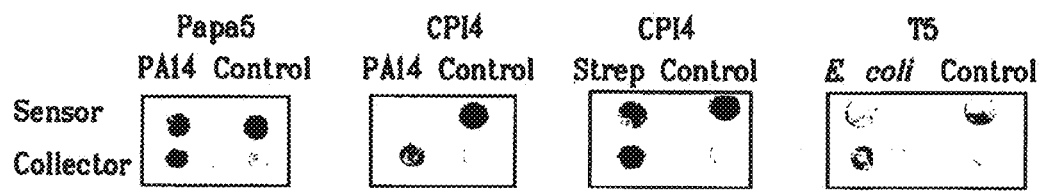
FIG. 13 includes photographs of sensors and collectors with cleaved labeled peptides on the surface.

The CPI4 and Papa5 peptides on the negatively charged sensor membrane were cleaved with *Pseudomonas aeruginosa* (PA14) and the T5 peptide was cleaved with *Escherichia coli* at ~37° C. The CPI4 peptide on the negatively charged sensor membrane was also cleaved with *Streptococcus pyogenes*. The peptide cleaved off of the surface of the sensors was designed to contain the dye component and was collected with a separate positively charged membrane (membrane SB-6407, available from Pall Corporation, East Hills, N.Y.). This interaction created a color change from white to blue on the collector membrane. Control samples consisted of collector membranes added to the sensor with PBS only. The experimental results are shown in FIG. 13. A color change on the collector membranes was obtained with bacteria when compared to controls for all the peptides describe above.

Figure 14:
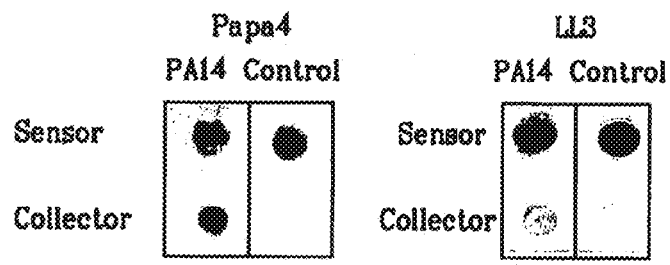
FIG. 14 includes photographs of sensors and collectors with cleaved labeled peptides on the surface.

In another embodiment, Reactive Black 5 labeled peptides were adsorbed onto P4 paper membranes (available from Fisher Scientific International Inc., Hampton, N.H.) following the same protocol as described above. The peptides that were used were Papa4 and LL3 which both contain histidine tags. The Papa4 and LL3 P4 membrane sensors were both cleaved with *Pseudomonas aeruginosa* (PA14) at ~37° C. and the cleaved portion of the peptide were collected on a SB-6407 membrane. The control consisted of the addition of PBS only to the sensor membranes. The results are shown in FIG. 14. A color change on the collector membranes was obtained with bacteria when compared to controls for all the peptides describe above.

Example 3

Labeling of Peptides with Reactive Dyes

Many of the peptide substrates were labeled with reactive dyes. Vinyl sulfone dyes were used to target cysteine groups on the peptides. Mono- and di-chlorotriazine dyes were used to target serine groups on the peptides. Sulfonyl chloride and N-hydroxysulfosuccinimidly (sulfo-NHS) ester dyes were used to target amine groups on the peptides.

An example of a labeling procedure for the labeling of the peptide CPI4 with Reactive Black 5 is shown in Table 1. CPI4 contains two cysteine groups that are targeted by Reactive Black 5 (a REMAZOL® dye) under basic conditions. The table below demonstrates that different levels of labeling (as evidenced by the dye-to-peptide ratio) can be obtained by varying the labeling conditions. The peptide was at ~5 mg/ml in water, Reactive Black 5 was at ~5 mg/ml in water, and the $Na_2CO_3$ was at ~10 mg/ml in water. Labeling was ~18 hours at ~37° C.

TABLE 1

| Peptide (uL) | Dye (uL) | $Na_2CO_3$ (uL) | Dye-to-Peptide Ratio |
|---|---|---|---|
| 100 | 300 | 60 | 2.0 |
| 100 | 300 | 80 | 1.9 |
| 100 | 300 | 100 | 1.6 |
| 100 | 200 | 100 | 0.9 |
| 100 | 100 | 100 | 0.6 |

Peptide labeling with triazine dyes were also performed under basic conditions. The triazine dyes target serine groups preferentially. The results in Table 2 were obtained under one set of reaction conditions for each dye. The peptide was at ~5 mg/ml in water, dyes were at ~10 mg/ml in water, and the $Na_2CO_3$ was at ~10 mg/ml in water. Labeling was 18 hours at ~37° C.

TABLE 2

| Peptide | Peptide (uL) | Dye | Dye (uL) | Na$_2$CO$_3$ (uL) | Dye-to-Peptide Ratio |
|---|---|---|---|---|---|
| JMH003 | 100 | Reactive Yellow 86 | 100 | 15 | 0.56 |
| JMH003 | 100 | CIBACRON™ Brilliant Yellow 3G-P | 100 | 80 | 0.21 |
| JMH001 | 100 | Reactive Blue 4 | 100 | 30 | 1.19 |
| JMH001 | 100 | Reactive Red 2 | 100 | 100 | 0.66 |

Table 2 demonstrates that it is possible to label the peptides with many different triazine dyes to obtain different colors. The labeling conditions can be improved, as shown in Table 1 for each of these dyes depending on the specific use and desired dye/peptide ratio.

Example 4

Dual Labeled Peptides

This example is directed towards an embodiment of the invention where the substrate includes at least two colorimetric components. The peptide includes two target amino acids for labeling with two colored dyes. Protecting groups are not required if the dyes target two different amino acids, for instance serine and cysteine. Reacting the peptide with one of the colored dyes, purifying it, concentrating it, and then reacting it with the second colored dye can perform labeling. Labeling can also be performed by reaction with both of the colored dyes targeting different amino acids at the same time and then purifying it and concentrating it.

The peptide JMH001 was used. A blue colored dye (e.g., Reactive Black 5, which is a REMAZOL® dye) was used to target the cysteine group at one end of the peptide and a yellow colored dye (e.g.; Reactive Yellow 86, which is a triazine dye) was used to target the serine group at the other end of the peptide. This particular reactive was done in two steps. The Reactive Black 5 was reacted with JMH001 in pH ~10 carbonate buffer with about a 2-5 molar excess of dye-to-peptide. After purification, the labeled peptide was reacted with Reactive Yellow 86 with about a 5 molar excess of the dye and Na$_2$CO$_3$. The Reactive Black 5-labeled JMH001 (center tube) illustrated a blue color prior to labeling with Reactive Yellow 86. The purified dual labeled peptide (JMH001 with Reactive Black 5 and Reactive Yellow 86) illustrated a green color.

Figure 15:
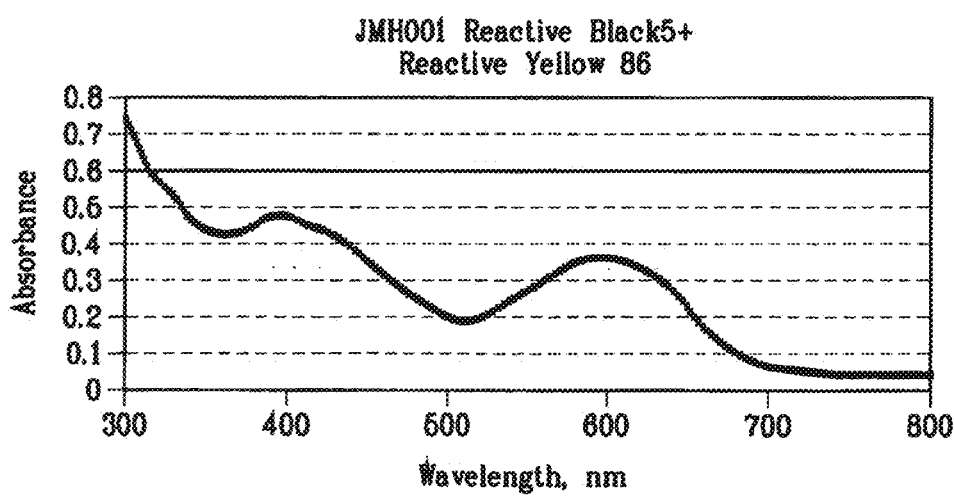
FIG. 15 shows a graph of the UV/visible spectrum in water of a dual-labeled peptide.

FIG. 15 shows the UV/visible spectrum of dual labeled JMH001. The Reactive Black 5 absorbance maximum is seen at ~595 nm and the Reactive Yellow 86 absorbance maximum is seen at approximately ~400 nm. The dye-to-peptide calculations for this particular labeling were ~0.4 for Reactive Black 5 and ~1.4 for Reactive Yellow 86. The dye to protein ratio above ~1.0 for Reactive Yellow 86 may be due to a difference of extinction coefficient since it was used in an unpurified form. For example, a high level of labeling of Reactive Black 5 may not produce a green color with highly labeled Reactive Yellow 86, since the reactive Black 5 has a larger extinction coefficient than the Reactive Yellow 86. For dual labeled peptides, the choice of the two dyes and the labeling conditions can be optimized to obtain the desired mixed color of the two.

Example 5

Cleavage of Dual Labeled Peptides

The peptide CPI3 was labeled with both Reactive Black 5 and CIBACRON™ Brilliant Yellow 3G-P creating a light blue colored peptide on P4 paper. By varying the labeling levels of Reactive Black 5 and CIBACRON™ Brilliant Yellow 3G-P, a more green-colored peptide could be produced. The dual labeled CPI3 peptide was adsorbed onto P4 paper and rinsed extensively. Positively charged membranes (membrane SB6407, available from Pall Corporation, East Hills, N.Y.) were placed on either side of the P4 membrane to draw off any loosely adsorbed material. After the membrane was fully rinsed, dual labeled CPI3 on P4 was placed in ~100 µl PBS with a dye collector membrane (membrane SB6407, available from Pall Corporation, East Hills, N.Y.) as a control. Dual labeled CPI3 on P4 was placed in ~75 µl PBS with ~25 µl overnight grown *Pseudomonas aeruginosa* (PA14) with a dye collector membrane (membrane SB6407, available from Pall Corporation, East Hills, N.Y.). The samples were left for ~18 hours at ~37° C. The dye collectormembrane of the dual-labeled CPI3/P4 membrane exposed to bacteria showed a color change while the control collector membrane remained white. The collector membrane of the sample exposed to bacteria appeared to show both blue and yellow dyes so it was likely that both cleaved portions of the CPI3 peptide migrated to the membrane or that the yellow portion of the peptide remained behind on, the P4 paper, but was very light in color. When the same dual-labeled CPI3 substrate was attached by its histidine tag to NTA resin and cleaved with PA14, the collector membrane showed a blue color while the NTA resin also showed some remaining blue color with a tint of yellow.

Example 6

Colorimetric Component on the Peptide and Support

In some embodiments, both the substrate and the solid support include colorimetric components. In further embodiments, upon cleavage of the peptide, the cleaved portion of the peptide that included a colorimetric component is removed and the remaining dye color can be seen on the support. In this manner, the modification of the substrate will produce a visible signal that includes a change of color from that of the mixed dye to that of the solid support. Optionally, the signal includes capturing the cleaved portion of the peptide on a collector. In this manner, two signals are produced by the modification; one expressed on the solid support and one expressed on the collector.

To illustrates this two-dye embodiment, amine labeled P4 paper was dyed with Lissamine Rhodamine B sulfonyl chloride and with dabsyl chloride to create pink and yellow membranes, respectively. Briefly, ~10 µl of a ~5 mg/ml dye solution in dimethyl formamide (DMF) was added to ~190 µl DMF and reacted with the amine labeled P4 paper overnight at room temperature. After extensive rinsing and dye removal with positively charged SB-6407 membranes, CPI4 labeled with Reactive Black 5 (dye/peptide ratio of 2.0) was adsorbed onto the membrane from a ~5 µl in ~95 µl PBS solution overnight at room temperature. After extensive rinsing and dye removal with positively charged SB-6407 membranes, the resulting membranes showed the mixed color of purple (created by a mixture of blue and pink) and dark green (created by a mixture of blue and yellow).

Example 7

Sterilization and Operation of Sensors

Peptides were prepared via standard Fmoc/Boc coupling chemistry on 2-chlorotrityl chloride resin (a "super-acid-sensitive" resin available from Bachem, Bubendorf, Switzerland). In this methodology, peptides are prepared using α-N 9-fluorenylmethyloxycarbonyl (Fmoc) protected amino acids; side chain functional groups are protected mainly with butoxyoxycarbonyl (Boc) or tert-butyl (t-Bu) groups, although other acid-sensitive protective groups can also be used. Peptides are grown from a bead via stepwise addition of amino acids to the surface. The amino carboxylic acid moiety is first coupled to a free reactive group (typically an amine) on the bead surface, giving an amide linkage. The base-sensitive Fmoc groups are removed in a 30% solution of piperidine in dimethylformamide (DMF) for 20 minutes, the beads are extensively washed, and the next amino acid introduced. Continuation of this process results in the construction of the desired polyamide structure grown from the beads from the C-terminus up to the N-terminus.

Upon Fmoc deprotection of the final amino acid, the resin was then reacted with Lissamine Rhodamine B containing a sulfonyl chloride group. Sulfonyl chlorides react rapidly with primary amine groups, giving a sulfonamide. Free unreacted dye was removed by extensive washings with DMF, acetone, and isopropanol. Once the washings were free of dye, the side-chain-protected peptide was decoupled from the bead in a 1% solution of trifluoroacetic acid (TFA) in dichloromethane (DCM). 2-Chlorotrityl chloride resin will liberate peptides in very low concentrations of acid. Typically, peptides are grown from Wang-type resins under very acidic conditions (~80-100% TFA); these conditions will not only decouple the peptide from the bead, but will also deprotect the side-groups of the peptide. In this case, use of 1% TFA in DCM was sufficient to decouple the dye-labeled peptide from the bead without any noticeable loss of side-chain protective groups. This gives a large molecule with only one reactive carboxylic acid functional group at the C-terminus. This protected labeled peptide was then reacted onto amine-labeled paper using the same coupling procedure as that used for preparing the peptide backbone. These peptide papers were then fully deprotected using 85% TFA, 5% water, 5% thioanisole, and 5% phenol, giving an active peptide sensor labeled with a pink dye.

Figure 16:
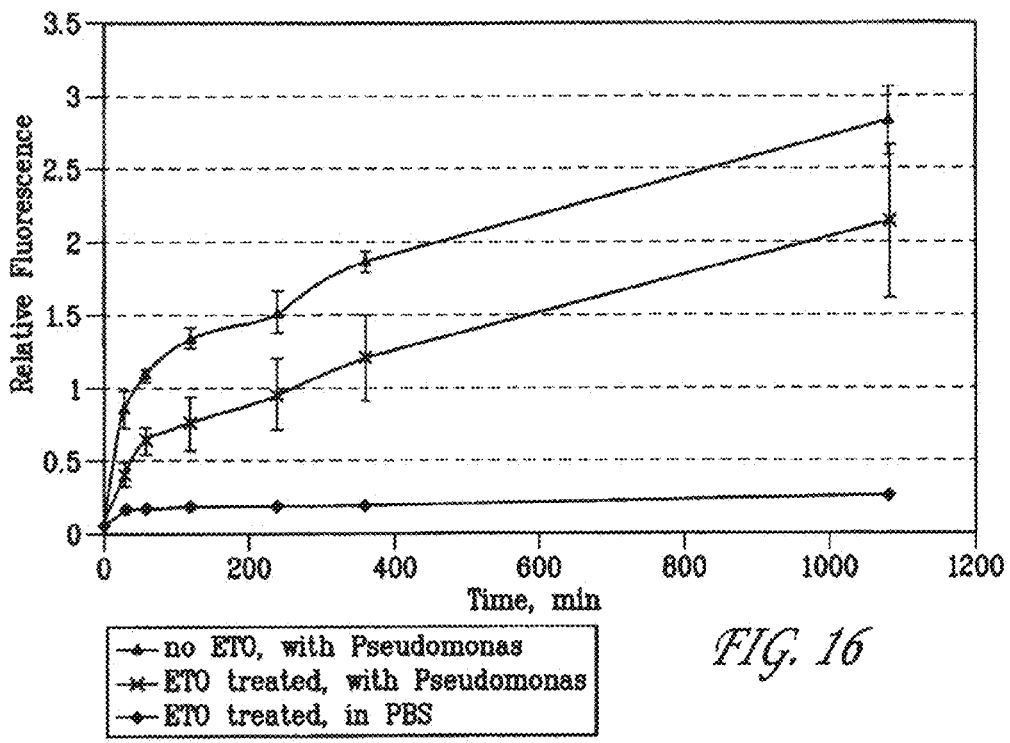
FIG. 16 illustrates a graph of the relative fluorescence of various sensors, wherein the sensors have been sterilized with ethylene oxide (ETO) and/or exposed to *Pseudomonas*.
Figure 17:
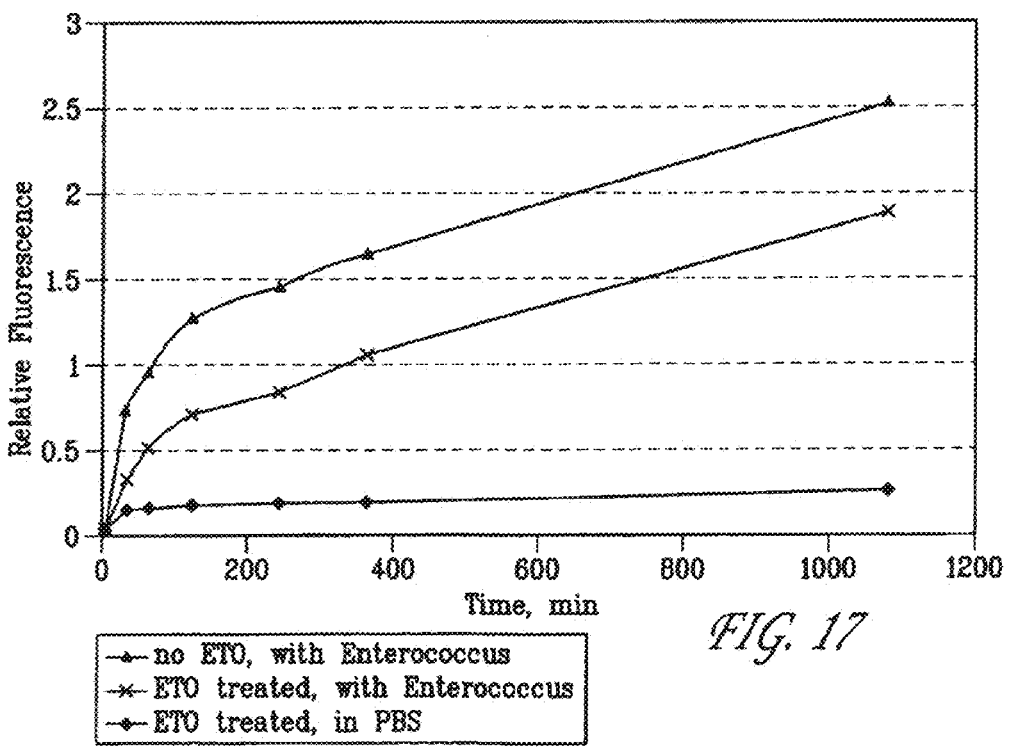
FIG. 17 illustrates a graph of the relative fluorescence of various sensors, wherein the sensors have been sterilized with ethylene oxide (ETO) and/or exposed to *Enterococcus*.

Samples were sterilized with ethylene oxide (ETO) under conditions commonly used for catheter sterilization. Although the signal was diminished by about 21% after ETO sterilization, the dye conjugate had the same reaction kinetics in the presence of *Pseudomonas* or *Enterococcus*, as shown in FIGS. 16 and 17, respectively. This shows that the sensors can be sterilized using ETO without a significant reduction in the sensitivity or reactivity with bacterial extracts. One very interesting observation is that the samples treated with ethylene oxide had lower background signals. This indicates that the sterilization process reduced the leaching of unincorporated dye.

Example 8

Push-Through Assay

The CPI3 peptide is a 5-histidine tagged version of the broad spectrum peptide CPI2 used for the detection of multiple pathogens. A cysteine group is was added on the N-terminal end to allow for labeling with dye:
CPI3    [Ac]-CGAMFLEAIPMSIPAAAHHHHH-[OH] (SEQ ID NO: 23).

The CPI3 peptide was labeled with tetramethylrhodamine iodoacetamide (TMRIA) dye (available from Molecular Probes, Eugene, Oreg.) on the cysteine group. The labeling reaction was performed in PBS pH 7.4 with an excess of TMRIA dye. The dye to peptide ratio was calculated to be about 1.0.

Approximately 1 mg of CPI3 labeled with TMRIA dye was bound to 1 ml nickel-nitrilotriacetic acid (Ni-NTA) agarose beads (obtained from Qiagen, Valencia, Calif.) through the 5-histidine tag on the peptide. Essentially all the CPI3 bound to the Ni-NTA beads, as evidenced by the loss of color from the solution.

A 50 μl bead volume of CPI3-TMRIA was placed in tubes and 200 μl of $1 \times 10^4$ or $1 \times 10^5$ cfu per mL *Enterococcus faecalis* was added and allowed to incubate for 5 minutes at room temperature. The bacterial proteases cleaved the CPI3 such that a dye-peptide fragment was released from the Ni-NTA beads. The beads were separated from solution through a short centrifugation with a microfuge. Corresponding volumes and bacterial concentrations (e.g. 100 μl of $1 \times 10^5$ cfu/μl) to obtain $10^5$, $10^6$, $10^7$ cfu equivalents were removed from the tubes and placed in the tip of a 1 ml syringe. Phosphate buffered saline with no added bacteria was used as a control. The syringe was then placed on top of a matching sized O-ring on a polyvinylidene fluoride (PVDF) membrane backed by filter paper and the plunger depressed to force the liquid through the membrane. Dye-peptide fragments were retained at the surface of the PVDF membrane and only un-dyed liquid passed through to the filter paper. After 5 minutes, the PVDF membrane exposed to the $10^7$ cfu/mL liquid exhibited the brightest color response, while the PVDF membrane exposed to the $10^6$ cfu/mL liquid exhibited less of a color response than the membrane exposed to the $10^7$ cfu/mL liquid. After 5 minutes, the PVDF membrane exposed to the $10^5$ cfu/mL liquid exhibited less of a color response than the membrane exposed to the $10^6$ cfu/mL liquid, while the membrane exprosed to the 0 cfu/mL liquid exhibited no discernable color response.

Example 9

SAP2

Sensors that include SAP2 were incubated in the presence of *Staphylococcus aureus, Pseudomonas aeruginosa, Streptococcus pyogenes, Escherichia coli*, and *Enterococcus faecalis* at 37° C. for 60 minutes. Fluorescence resonance energy transfer (FRET) with an excitation of 340 and an emission 490 nm was used to measure the resulting signal strength. Only the *Staphylococcus aureus* sample was able to hydrolyze the peptide thereby activating the quenched fluorescence of the EDANS molecule. This indicates that SAP2 is suitable for use in sensors that can specifically detect the presence of *Staphylococcus aureus*.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of detecting the presence or absence of a pathogenic microorganism of interest in a sample by detecting the modification of a substrate exposed to said sample, said method comprising the steps of:

(a) exposing an unmodified substrate to a sample under conditions that will result in a modification of the substrate by a protein produced by any of said pathogenic microorganism of interest which may be present in said sample, the unmodified substrate including a peptide and a first colorimetric component, the first colorimetric component being coupled to the peptide, wherein the peptide includes at least one member of the group consisting of the peptide sequence LLGDFFRKSKEKIGKEFKRIVXRIKOFLRNLVPRTES (SEQ ID NO: 1), the peptide sequence KKASEAAHKSALKSAE (SEQ ID NO: 3), the peptide sequence CHHHASEAAHKSALKSAE (SEQ ID NO: 4), the peptide sequence KHLGGGALGGGAKE (SEQ ID NO: 5), the peptide sequence KHLGGGGGAKE (SEQ ID NO: 6), the peptide sequence ACCDEYLQTKE (SEQ ID NO: 7), the peptide sequence ADTVEPTGAKE (SEQ ID NO: 8), the peptide sequence KLPHKLSWSADNP (SEQ ID NO: 9), the peptide sequence PVPSTPPTPSPSTP (SEQ ID NO: 10), the peptide sequence NMLSEVERE (SEQ ID NO: 11), the peptide sequence KQNMLSEVERADTE (SEQ ID NO: 12), the peptide sequence NEAIQEDQVQYE (SEQ ID NO: 13), the peptide sequence ETKVEENEAIQK (SEQ ID NO: 14), the peptide sequence OSRPVRRRRRRPRVSK (SEQ ID NO: 15), the peptide sequence KVSRRRRRGGD (SEQ ID NO: 16), the peptide sequence KKASEVSRRRRRGGK (SEQ ID NO: 17), the peptide sequence CHHHASEVSRRRRRGGK (SEQ ID NO: 18), the peptide sequence KEKIGKEFKRIVQE (SEQ ID NO: 19), the peptide sequence KVQRIKOFLRNLVE (SEQ ID NO: 20), the peptide sequence EAAGAMFLEAIPK (SEQ ID NO: 21), the peptide sequence EGAMFLEAIPMSIPK (SEQ ID NO: 22), the peptide sequence CGAMFLEAIPMSIPAAAHHHHH (SEQ ID NO: 23), the peptide sequence KARRRRGGGAMFLEAIPMSIPCGC (SEQ ID NO: 24), the peptide sequence VSRRRRRGGDGDGC (SEQ ID NO: 25), the peptide sequence GGDGDGC (SEQ ID NO: 26), the peptide sequence VSRRRRRGGDGKGDAC (SEQ ID NO: 27), the peptide sequence NEAIQEDQVQARRAKARRAC (SEQ ID NO: 28), the peptide sequence QVQARRAKARRAC (SEQ ID NO: 29), the peptide sequence GGDGKGDAC (SEQ ID NO: 30), the peptide sequence QVQARRRAKARRRAC (SEQ ID NO: 31), the peptide sequence VSRRRRRGGKGC (SEQ ID NO: 32), the peptide sequence SVTRRRRRGGRASGGC (SEQ ID NO: 33), the peptide sequence SEAIQEDQVQYCAAAHHHHH (SEQ ID NO: 34), the peptide sequence KARRRRRGGDGDGCGC (SEQ ID NO: 35), the peptide sequence HHHHHSRRRRRGGCGC (SEQ ID NO: 36), the peptide sequence HHHHHSVQRIKDFLRNLVCGC (SEQ ID NO: 37), the peptide sequence RRRRRSVQRIKDFLRNLVCGC (SEQ ID NO: 38), the peptide sequence HHHHHAAHKSALKSACGC (SEQ ID NO: 39), the peptide sequence RRRRRAAHKSALKSACGC (SEQ ID NO: 40), the peptide sequence PGTKLYTVPW (SEQ ID NO: 41), an Alt derived peptide, and a peptidoglycans; and (b) detecting a modification of the substrate or an absence of the modification of the substrate, wherein the modification comprises cleaving a portion of the peptide comprising the first colorimetric component from the substrate and results in a visible color change which is perceptible without any kind of detection equipment or enhancement equipment; wherein the peptide component of the substrate has an amino acid sequence which permits said substrate to specifically and uniquely react with said protein produced by said pathogenic microorganism of interest; and wherein said first colorimetric component comprises a reactive dye approved for use in foods, drugs, cosmetics or medical devices by the U.S. Food & Drug Administration, thereby detecting the presence or absence of a pathogenic microorganism of interest.

2. A method according to claim 1, wherein the first colorimetric component is covalently bonded to the peptide.

3. A method according to claim 1, wherein the modification includes hydrolysis of a peptide bond and results in a portion of the peptide detaching from the substrate.

4. A method according to claim 1, wherein the first colorimetric component is one of the members of the group consisting of a dye; a reactive dye; a fiber reactive dye; a dye suitable for use in a contact lens; a dye suitable for use in a suture; a monohalogentriazine dye; a dihalogentriazine dye; a 2,4,5 trihalogenopyriminidine dye; a 2,3 dihaloquinoxaline dye; a N-hydroxysulfosuccinimidyl a (sulfo-NHS) ester functionalized dye; a N-hydroxysuccinimidyl(NHS) functionalized dye; a vinyl sulfone dye; a sulfonylchloride dye; a tetrafluorophenyl ester functionalized dye; an isothiocyanate functionalized dye; and an iodoacetyl functionalized dyes.

5. A method according to claim 1, wherein the visible color change is a loss of color.

6. A method according to claim 1, wherein the unmodified substrate further includes a second colorimetric component that is dissimilar to the first colorimetric component.

7. A method according to claim 1, wherein the peptide is coupled to a solid support.

8. A method according to claim 7, wherein the modification of the substrate results in a hue of the solid support becoming more visible.

9. A method according to claim 7, wherein the peptide is covalently attached to the solid support.

10. A method according to claim 7, wherein the solid support is selected from the group consisting of a wound dressing, a sterilized material, an article that contains the sample, an article that collects the sample, a polymer, a membrane, a resin, glass, a sponge, a disk, a scope, a filter, a lens, a foam, a cloth, a paper, a suture, and a bag.

11. A method according to claim 1, wherein the sample is at least one of the group consisting of a wound surface on a subject, a body fluid, a piece of hair, a piece of nail, a piece of shell, a piece of scale, a piece of feather, a piece of tissue, an article implanted in the body of an animal, catheter, a urine collection bag, a blood collection bag, a plasma collection bag, a disk, a scope, a filter, a lens, foam, cloth, paper, a suture, a swab, a dipstick, a sponge, a polymeric article, an article made of a resin, a glass article, a test tube, a well of a microplate, a portion of contact lens solution, a sponge, a polymeric material, a membrane, an article made of resin, an article made of glass, and a swab.

12. A method according to claim 1, wherein modification of the substrate results in the migration of the cleaved portion of the peptide toward a collector, the migration resulting in a visible color change.

13. A method according to claim 12, wherein the collector includes at least one material selected from the group consisting of a membrane, a resin, a polymer, a film, glass, or a chelating material.

14. A method according to claim 1, wherein modification of the substrate is used to indicate the presence of a bacterial enzyme selected from the group consisting of a lysin, an autolysin, a lipase, an exotoxin, a cell wall enzyme, a matrix binding enzyme, a protease, a hydrolase, a virulence factor enzyme, and a metabolic enzyme.

* * * * *

SEQUENCE LISTING

<160> NUMBER OF SEQ ID NOS: 41

<210> SEQ ID NO 1
<211> LENGTH: 37
<212> TYPE: PRT
<213> ORGANISM: Artificial Sequence
<220> FEATURE:
<223> OTHER INFORMATION: Synthetic Peptide Sequence
<220> FEATURE:
<221> NAME/KEY: VARIANT
<222> LOCATION: 22
<223> OTHER INFORMATION: Xaa = Any Amino Acid

<400> SEQUENCE: 1

Leu Leu Gly Asp Phe Phe Arg Lys Ser Lys Glu Lys Ile Gly Lys Glu
 1               5                  10                  15

Phe Lys Arg Ile Val Xaa Arg Ile Lys Asp Phe Leu Arg Asn Leu Val
             20                  25                  30

Pro Arg Thr Glu Ser
         35

<210> SEQ ID NO 2
<211> LENGTH: 12
<212> TYPE: PRT
<213> ORGANISM: Artificial Sequence
<220> FEATURE:
<223> OTHER INFORMATION: Synthetic Peptide Sequence

<400> SEQUENCE: 2

Lys Ala Ala His Lys Ser Ala Leu Lys Ser Ala Glu
 1               5                  10

<210> SEQ ID NO 3
<211> LENGTH: 16
<212> TYPE: PRT
<213> ORGANISM: Artificial Sequence
<220> FEATURE:
<223> OTHER INFORMATION: Synthetic Peptide Sequence

<400> SEQUENCE: 3

Lys Lys Ala Ser Glu Ala Ala His Lys Ser Ala Leu Lys Ser Ala Glu
 1               5                  10                  15

<210> SEQ ID NO 4
<211> LENGTH: 18
<212> TYPE: PRT
<213> ORGANISM: Artificial Sequence
<220> FEATURE:
<223> OTHER INFORMATION: Synthetic Peptide Sequence

<400> SEQUENCE: 4

Cys His His His Ala Ser Glu Ala Ala His Lys Ser Ala Leu Lys Ser
 1               5                  10                  15

Ala Glu

<210> SEQ ID NO 5
<211> LENGTH: 14
<212> TYPE: PRT
<213> ORGANISM: Artificial Sequence
<220> FEATURE:
<223> OTHER INFORMATION: Synthetic Peptide Sequence

<400> SEQUENCE: 5

Lys His Leu Gly Gly Gly Ala Leu Gly Gly Gly Ala Lys Glu
 1               5                  10

<210> SEQ ID NO 6
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 6

Lys His Leu Gly Gly Gly Gly Gly Ala Lys Glu
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 7

Ala Cys Cys Asp Glu Tyr Leu Gln Thr Lys Glu
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 8

Ala Asp Thr Val Glu Pro Thr Gly Ala Lys Glu
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic Peptide Sequence

<400> SEQUENCE: 9

Lys Leu Pro His Lys Leu Ser Trp Ser Ala Asp Asn Pro
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic Peptide Sequence

<400> SEQUENCE: 10

Pro Val Pro Ser Thr Pro Pro Thr Pro Ser Pro Ser Thr Pro
1               5                   10

<210> SEQ ID NO 11
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 11

Asn Met Leu Ser Glu Val Glu Arg Glu
1               5

```
<210> SEQ ID NO 12
<211> LENGTH: 14
<212> TYPE: PRT
<213> ORGANISM: Artificial Sequence
<220> FEATURE:
<223> OTHER INFORMATION: Synthetic Peptide Sequence

<400> SEQUENCE: 12

Lys Gln Asn Met Leu Ser Glu Val Glu Arg Ala Asp Thr Glu
 1               5                  10

<210> SEQ ID NO 13
<211> LENGTH: 12
<212> TYPE: PRT
<213> ORGANISM: Artificial Sequence
<220> FEATURE:
<223> OTHER INFORMATION: Synthetic Peptide Sequence

<400> SEQUENCE: 13

Asn Glu Ala Ile Gln Glu Asp Gln Val Gln Tyr Glu
 1               5                  10

<210> SEQ ID NO 14
<211> LENGTH: 12
<212> TYPE: PRT
<213> ORGANISM: Artificial Sequence
<220> FEATURE:
<223> OTHER INFORMATION: Synthetic Peptide Sequence

<400> SEQUENCE: 14

Glu Thr Lys Val Glu Glu Asn Glu Ala Ile Gln Lys
 1               5                  10

<210> SEQ ID NO 15
<211> LENGTH: 15
<212> TYPE: PRT
<213> ORGANISM: Artificial Sequence
<220> FEATURE:
<223> OTHER INFORMATION: Synthetic Peptide Sequence

<400> SEQUENCE: 15

Asp Ser Arg Pro Val Arg Arg Arg Arg Pro Arg Val Ser Lys
 1               5                  10                  15

<210> SEQ ID NO 16
<211> LENGTH: 11
<212> TYPE: PRT
<213> ORGANISM: Artificial Sequence
<220> FEATURE:
<223> OTHER INFORMATION: Synthetic Peptide Sequence

<400> SEQUENCE: 16

Lys Val Ser Arg Arg Arg Arg Arg Gly Gly Asp
 1               5                  10

<210> SEQ ID NO 17
<211> LENGTH: 15
<212> TYPE: PRT
<213> ORGANISM: Artificial Sequence
<220> FEATURE:
<223> OTHER INFORMATION: Synthetic Peptide Sequence

<400> SEQUENCE: 17

Lys Lys Ala Ser Glu Val Ser Arg Arg Arg Arg Gly Gly Lys
 1               5                  10                  15

<210> SEQ ID NO 18
```

```
<211> LENGTH: 17
<212> TYPE: PRT
<213> ORGANISM: Artificial Sequence
<220> FEATURE:
<223> OTHER INFORMATION: Synthetic Peptide Sequence

<400> SEQUENCE: 18

Cys His His His Ala Ser Glu Val Ser Arg Arg Arg Arg Arg Gly Gly
1               5                   10                  15

Lys

<210> SEQ ID NO 19
<211> LENGTH: 14
<212> TYPE: PRT
<213> ORGANISM: Artificial Sequence
<220> FEATURE:
<223> OTHER INFORMATION: Synthetic Peptide Sequence

<400> SEQUENCE: 19

Lys Glu Lys Ile Gly Lys Glu Phe Lys Arg Ile Val Gln Glu
1               5                   10

<210> SEQ ID NO 20
<211> LENGTH: 14
<212> TYPE: PRT
<213> ORGANISM: Artificial Sequence
<220> FEATURE:
<223> OTHER INFORMATION: Synthetic Peptide Sequence

<400> SEQUENCE: 20

Lys Val Gln Arg Ile Lys Asp Phe Leu Arg Asn Leu Val Glu
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Synthetic Peptide Sequence

<400> SEQUENCE: 21

Glu Ala Ala Gly Ala Met Phe Leu Glu Ala Ile Pro Lys
1               5                   10

<210> SEQ ID NO 22
<211> LENGTH: 15
<212> TYPE: PRT
<213> ORGANISM: Artificial Sequence
<220> FEATURE:
<223> OTHER INFORMATION: Synthetic Peptide Sequence

<400> SEQUENCE: 22

Glu Gly Ala Met Phe Leu Glu Ala Ile Pro Met Ser Ile Pro Lys
1               5                   10                  15

<210> SEQ ID NO 23
<211> LENGTH: 22
<212> TYPE: PRT
<213> ORGANISM: Artificial Sequence
<220> FEATURE:
<223> OTHER INFORMATION: Synthetic Peptide Sequence

<400> SEQUENCE: 23

Cys Gly Ala Met Phe Leu Glu Ala Ile Pro Met Ser Ile Pro Ala Ala
1               5                   10                  15

Ala His His His His His
```

```
                          20

<210> SEQ ID NO 24
<211> LENGTH: 25
<212> TYPE: PRT
<213> ORGANISM: Artificial Sequence
<220> FEATURE:
<223> OTHER INFORMATION: Synthetic Peptide Sequence

<400> SEQUENCE: 24

Lys Ala Arg Arg Arg Arg Gly Gly Gly Ala Met Phe Leu Glu Ala
 1               5                  10                  15

Ile Pro Met Ser Ile Pro Cys Gly Cys
            20                  25

<210> SEQ ID NO 25
<211> LENGTH: 14
<212> TYPE: PRT
<213> ORGANISM: Artificial Sequence
<220> FEATURE:
<223> OTHER INFORMATION: Synthetic Peptide Sequence

<400> SEQUENCE: 25

Val Ser Arg Arg Arg Arg Arg Gly Gly Asp Gly Asp Gly Cys
 1               5                  10

<210> SEQ ID NO 26
<211> LENGTH: 7
<212> TYPE: PRT
<213> ORGANISM: Artificial Sequence
<220> FEATURE:
<223> OTHER INFORMATION: Synthetic Peptide Sequence

<400> SEQUENCE: 26

Gly Gly Asp Gly Asp Gly Cys
 1               5

<210> SEQ ID NO 27
<211> LENGTH: 16
<212> TYPE: PRT
<213> ORGANISM: Artificial Sequence
<220> FEATURE:
<223> OTHER INFORMATION: Synthetic Peptide Sequence

<400> SEQUENCE: 27

Val Ser Arg Arg Arg Arg Arg Gly Gly Asp Gly Lys Gly Asp Ala Cys
 1               5                  10                  15

<210> SEQ ID NO 28
<211> LENGTH: 20
<212> TYPE: PRT
<213> ORGANISM: Artificial Sequence
<220> FEATURE:
<223> OTHER INFORMATION: Synthetic Peptide Sequence

<400> SEQUENCE: 28

Asn Glu Ala Ile Gln Glu Asp Gln Val Gln Ala Arg Arg Ala Lys Ala
 1               5                  10                  15

Arg Arg Ala Cys
            20

<210> SEQ ID NO 29
<211> LENGTH: 13
<212> TYPE: PRT
<213> ORGANISM: Artificial Sequence
<220> FEATURE:
```

```
<223> OTHER INFORMATION: Synthetic Peptide Sequence

<400> SEQUENCE: 29

Gln Val Gln Ala Arg Arg Ala Lys Ala Arg Arg Ala Cys
1               5                   10

<210> SEQ ID NO 30
<211> LENGTH: 9
<212> TYPE: PRT
<213> ORGANISM: Artificial Sequence
<220> FEATURE:
<223> OTHER INFORMATION: Synthetic Peptide Sequence

<400> SEQUENCE: 30

Gly Gly Asp Gly Lys Gly Asp Ala Cys
1               5

<210> SEQ ID NO 31
<211> LENGTH: 15
<212> TYPE: PRT
<213> ORGANISM: Artificial Sequence
<220> FEATURE:
<223> OTHER INFORMATION: Synthetic Peptide Sequence

<400> SEQUENCE: 31

Gln Val Gln Ala Arg Arg Arg Ala Lys Ala Arg Arg Arg Ala Cys
1               5                   10                  15

<210> SEQ ID NO 32
<211> LENGTH: 12
<212> TYPE: PRT
<213> ORGANISM: Artificial Sequence
<220> FEATURE:
<223> OTHER INFORMATION: Synthetic Peptide Sequence

<400> SEQUENCE: 32

Val Ser Arg Arg Arg Arg Arg Gly Gly Lys Gly Cys
1               5                   10

<210> SEQ ID NO 33
<211> LENGTH: 16
<212> TYPE: PRT
<213> ORGANISM: Artificial Sequence
<220> FEATURE:
<223> OTHER INFORMATION: Synthetic Peptide Sequence

<400> SEQUENCE: 33

Ser Val Thr Arg Arg Arg Arg Arg Gly Gly Arg Ala Ser Gly Gly Cys
1               5                   10                  15

<210> SEQ ID NO 34
<211> LENGTH: 20
<212> TYPE: PRT
<213> ORGANISM: Artificial Sequence
<220> FEATURE:
<223> OTHER INFORMATION: Synthetic Peptide Sequence

<400> SEQUENCE: 34

Ser Glu Ala Ile Gln Glu Asp Gln Val Gln Tyr Cys Ala Ala Ala His
1               5                   10                  15

His His His His
            20

<210> SEQ ID NO 35
<211> LENGTH: 16
<212> TYPE: PRT
```

<213> ORGANISM: Artificial Sequence
<220> FEATURE:
<223> OTHER INFORMATION: Synthetic Peptide Sequence

<400> SEQUENCE: 35

Lys Ala Arg Arg Arg Arg Gly Gly Asp Gly Asp Gly Cys Gly Cys
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Synthetic Peptide Sequence

<400> SEQUENCE: 36

His His His His His Ser Arg Arg Arg Arg Gly Gly Cys Gly Cys
1               5                   10                  15

<210> SEQ ID NO 37
<211> LENGTH: 21
<212> TYPE: PRT
<213> ORGANISM: Artificial Sequence
<220> FEATURE:
<223> OTHER INFORMATION: Synthetic Peptide Sequence

<400> SEQUENCE: 37

His His His His His Ser Val Gln Arg Ile Lys Asp Phe Leu Arg Asn
1               5                   10                  15

Leu Val Cys Gly Cys
            20

<210> SEQ ID NO 38
<211> LENGTH: 21
<212> TYPE: PRT
<213> ORGANISM: Artificial Sequence
<220> FEATURE:
<223> OTHER INFORMATION: Synthetic Peptide Sequence

<400> SEQUENCE: 38

Arg Arg Arg Arg Arg Ser Val Gln Arg Ile Lys Asp Phe Leu Arg Asn
1               5                   10                  15

Leu Val Cys Gly Cys
            20

<210> SEQ ID NO 39
<211> LENGTH: 18
<212> TYPE: PRT
<213> ORGANISM: Artificial Sequence
<220> FEATURE:
<223> OTHER INFORMATION: Synthetic Peptide Sequence

<400> SEQUENCE: 39

His His His His His Ala Ala His Lys Ser Ala Leu Lys Ser Ala Cys
1               5                   10                  15

Gly Cys

<210> SEQ ID NO 40
<211> LENGTH: 18
<212> TYPE: PRT
<213> ORGANISM: Artificial Sequence
<220> FEATURE:
<223> OTHER INFORMATION: Synthetic Peptide Sequence

<400> SEQUENCE: 40

```
Arg Arg Arg Arg Arg Ala Ala His Lys Ser Ala Leu Lys Ser Ala Cys
 1               5                  10                  15

Gly Cys

<210> SEQ ID NO 41
<211> LENGTH: 10
<212> TYPE: PRT
<213> ORGANISM: Artificial Sequence
<220> FEATURE:
<223> OTHER INFORMATION: Synthetic Peptide Sequence

<400> SEQUENCE: 41

Pro Gly Thr Lys Leu Tyr Thr Val Pro Trp
 1               5                  10
```